(12) United States Patent
Nakajima et al.

(10) Patent No.: US 7,282,356 B2
(45) Date of Patent: Oct. 16, 2007

(54) D-AMINOACYLASE MUTANTS

(75) Inventors: Takanori Nakajima, Ibaraki (JP); Hiroaki Yamamoto, Ibaraki (JP)

(73) Assignee: Daicel Chemical Industries, Ltd. (JP)

( * ) Notice: Subject to any disclaimer, the term of this patent is extended or adjusted under 35 U.S.C. 154(b) by 419 days.

(21) Appl. No.: 10/746,796

(22) Filed: Dec. 23, 2003

(65) Prior Publication Data
US 2004/0197880 A1    Oct. 7, 2004

(30) Foreign Application Priority Data
Dec. 24, 2002   (JP)   ............................. 2002-372624

(51) Int. Cl.
*C12P 13/22*   (2006.01)
*C12N 9/78*    (2006.01)
*C12N 15/00*   (2006.01)
*C12N 1/20*    (2006.01)
*C07H 21/06*   (2006.01)

(52) U.S. Cl. .............. 435/108; 435/320.1; 435/252.31; 435/252.33; 435/252.34; 435/252.35; 435/254.1; 435/254.11; 435/227; 536/23.2

(58) Field of Classification Search ................ 435/227, 435/320.1, 108, 252.31, 252.33, 252.34, 435/252.35, 254.1, 254.11; 536/23.2
See application file for complete search history.

(56) References Cited

U.S. PATENT DOCUMENTS

| 2002/0151035 A1 | 10/2002 | Mitsuhashi et al. |
| 2003/0207436 A1 | 11/2003 | Osabe et al. |

FOREIGN PATENT DOCUMENTS

| EP | 1120465 | 8/2001 |
| EP | 1188823 | 3/2002 |
| JP | 64-5488 | 1/1989 |
| WO | WO 00/23598 A1 | 4/2000 |
| WO | WO 02/061077 A1 | 8/2002 |

OTHER PUBLICATIONS

Moriguchi, M., et al. "Production, purification, and characterization of D-aminoacylase from *Alcaligenes xylosoxydans* subsp. *Xylosoxydans* A-6." Biosci. Biotech. Biochem. 1993; 57(7):1149-52.
Wakayama M, et al. Overproduction of D-aminoacylase from Alcaligenes xylosoxydans subsp. xylosoxydans A-6 in *Escherichia coli* and its purification. Protein Expr Purif. Jun. 1996;7(4):395-9.
Wakayama M. et al., "Cloning and sequencing if a Gene Encoding D-Aminoacylase from *Alcaligenes xylosydans* subsp. *xylosoxydans* A-6 and Expression of the Gene in *Escherichia coli*," Biosci. Biotechnol. Biochem., vol 59(11) pp. 2115-2119 (1995).
Sakai K. et al., "Purification and Properties of D-Aminoacylase from *Alcaligenes dentrificans* subsp. *xylosoxydans* MI-4," Journal of Fermentation and Bioengineering. vol. 71(2) pp. 79-82 (1991).
WPI AN 2002-627481, 2002.

*Primary Examiner*—Rebecca E. Prouty
*Assistant Examiner*—Malgorzata A. Walicka
(74) *Attorney, Agent, or Firm*—Lahive & Cockfield, LLP.

(57) ABSTRACT

The present invention provides mutant D-aminoacylases and use thereof. The mutant D-aminoacylases are hard to be inhibited by the substrate and, comprise the amino acid sequences of the D-aminoacylase derived from *Alcaligenes denitrificans* subsp. *xylosoxydans* MI-4 strain, wherein amino acid residues at specific sites have been modified. The mutants of the present invention have high reaction specificity as well as resistance to inhibition by the substrate. The present invention enables high-yield production of D-amino acids using higher concentrations of N-acyl-DL-amino acid as the substrate. The mutants of the present invention are useful in producing D-tryptophan in particular.

8 Claims, 2 Drawing Sheets

US 7,282,356 B2

D-AMINOACYLASE MUTANTS

RELATED APPLICATIONS

This application claims benefit of prior-filed Japanese patent application 2002-372624 JP (filed Dec. 24, 2002) entitled "D-Aminoacylase Mutants." The entire content of the above-referenced application is incorporated herein by reference.

FIELD OF THE INVENTION

The present invention relates to mutants of D-aminoacylase, genes encoding the mutants, methods for producing them, and methods for producing D-amino acids, in particular D-tryptophan, using the D-aminoacylase mutants.

BACKGROUND OF THE INVENTION

An enzyme exhibits not only high catalytic activity but also specificity. Such specificity includes stereospecificity as well as substrate specificity and reaction specificity. The stereospecificity of an enzyme is almost absolute although there are some exceptions.

Recent studies have become more and more dependent on high precision technologies. In this context, it becomes increasingly important to use optically active isomers in the fields of pharmaceuticals, pesticides, feed, flavor, and others. Technologies to isolate specific optical isomers are exceedingly important because their physiological activities are sometimes quite distinct to each other. Thus, how to isolate (synthesize or resolve) optically pure enantiomers is an industrially important objective.

D-amino acids are non-proteinaceous amino acids and have been known to occur naturally in small cyclic peptides, peptide glycans in bacterial cell walls, and peptidic antibiotics over a long time. Recently, D-amino acids have been revealed to exist as a bound form in constituents of neuropeptides, dental enamel proteins, and proteins in crystalline lenses and in the brain, and thus many studies have been carried out to elucidate the physiologic significances of D-amino acids and enzymatic methods for synthesizing D-amino acids.

D-amino acids are widely used as important intermediates in the synthesis of pesticides, pharmaceuticals, and such. D-tryptophan is used as an intermediate in the synthesis of an agent to treat erectile dysfunction.

Previously established methods for producing D-amino acids include, for example, the following methods:

(1) A method that comprises chemically hydrolyzing 5-substituted hydantoin to produce a corresponding DL-amino acids and isolating a D-amino acid by optical resolution. (2) A method that comprises contacting 5-substituted hydantoin with a microorganism, its culture medium or its processed product, which is capable of producing an optically active D-N-carbamyl amino acid from 5-substituted hydantoin, and preparing a D-amino acid using sodium nitrite or D-carbamoylase (WO 94/03613). An alternative method comprises contacting 5-substituted hydantoin with a microorganism, its culture medium, or its processed product, which is capable of directly producing a D-amino acid from 5-substituted hydantoin. The following microorganisms can be used in this method:

The genus *Pseudomonas* (Unexamined Published Japanese Patent Application (JP-A) No. Sho 54-2398)

The genus *Moraxella* (JP-A No. Sho 54-89089)

The genus *Hansenula* (JP-A No. Sho 61-177991)

(3) A method that comprises reacting a DL-amino acid with a microorganism, its culture medium, or its processed product, which is capable of decomposing the L form, and recovering the residual D-amino acid (JP-A No. Hei 09-75097).

(4) A method that comprises contacting L-aminoacylase with an N-acetyl-DL-amino acid to hydrolyze, N-acetyl-L-amino acid which is one enantiomer of the DL-amino acid, recovering the residual N-acetyl-D-amino acid, and chemically hydrolyzing the N-acetyl -D-amino acid to produce a D-amino acid (Methods in Enzymology. 3, 554).

(5) A method that comprises contacting DL-amino acid amide with cells or a processed product of a microorganism having D-amidase or D-amidase activity that selectively hydrolyzes only the D form of DL-amino acid amide, to produce ad-amino acid (JP-A No. Hei 02-234678), or method that comprises contacting DL-amino acid amide with cells or a processed product of a microorganism having L-amidase or L-amidase activity that selectively hydrolyzes only the L form of DL-amino acid amide and chemically hydrolyzing the residual D-amino acid amide to produce a D-amino acid (JP-A No. Sho 57-013000).

(6) A method that comprises producing a D-amino acid from a corresponding α-keto acid by contacting D-amino acid transaminase with the α-keto acid in the presence of a D-amino acid as an amino group donor (JP-A No. Sho 62-205790).

(7) A method that comprises contacting DL-tryptophan with cells or a processed product of a microorganism having tryptophanase or tryptophanase activity that selectively decomposes L-tryptophan, and recovering the residual D-tryptophan (JP-A No. Hei 11-042097).

However, the methods described above have various problems, including high cost of materials, complicated processes, and low yields. Thus, with these methods, it is quite difficult to produce D-tryptophan in high yield and with low cost. In contrast to the methods described above, the following D-amino acid production method is known.

(8) A method that comprises contacting D-aminoacylase with an N-acetyl-DL-amino acid to hydrolyze only an N-acetyl-D-amino acid which is one enantiomer of the DL-amino acid, thereby producing a D-amino acid (JP-A No. Sho 53-059092).

With this method, D-tryptophan can be produced by a single-step enzymatic reaction using N-acetyl-DL-tryptophan as a starting material, which is synthesized from inexpensive L-tryptophan and acetic anhydride.

Examples of known microorganisms that produce D-aminoacylase include the following:

The genus *Pseudomonas*:

*Pseudomonas* sp. AAA6029 (Chem. Pharm. Bull., 26, 2698(1978));

*Pseudomonas* sp. 1158 (J. Antibiot., 33, 550 (1980));

*Pseudomonas* sp. 5f-1 (Appl. Environ. Microbiol. 57, 2540(1991));

The genus *Streptomyces*:

*Streptomyces olivaceus* (Argric. Biol. Chem., 42, 107 (1978));

*Streptomyces olivaceus* 62-3 (Argric. Biol. Chem., 44, 1089(1980));

*Streptomyces olivaceus* S-62 (JP-A No. Sho 53-59092);

*Streptomyces thermonitrificans* CS5-9 (JP-A No. 2002-45179);

The genus *Alcaligenes*:

*Alcaligenes denitrificans* subsp. *denitrificans* DA181 (Appl. Environ. Microbiol., 54, 984(1988));

*Alcaligenes faecalis* DA1 (Appl. Environ. Microbiol., 57, 1259(1991));

*Alcaligenes xylosoxidans* subsp. *xylosoxydans* A-6 having an enzyme acting on acidic N-acyl-D-amino acids (FEBS, 289, 44(1991), Biosci. Biotech. Biochem., 57, 1145(1993)) and an enzyme acting on neutral N-acyl-D-amino acids (Biosci. Biotech. Biochem., 57, 1149(1993));

*Alcaligenes denitrificans* subsp. *xylosoxydans* MI-4 (J. Ferment. Bioeng., 71, 79 (1991));

*Alcaligenes* sp. (WO 00/23598);

Others:

*Stenotrophomonas maltophilia* (J. Industrial Microbiol. Biotechnol., 21, 296(1998))

*Arthrobacter hydrocarboglutamicus* (JP-A No. Hei 11-113592)

*Amycolatopsis orientaris* (JP-A No. Hei 11-98982)

*Sebekia benihana* (JP-A No. Hei 11-318442)

*Hypomyces mycophilus* (JP-A No. 2000-41684)

*Rhodococcus rhodochrous*

*Pimelobacter simplex* (JP-A No. Hei 06-22789),

*Methylobacterium mesophilicum*

*Nocardioides thermolilacinus* (WO 02/061077)

*Trichoderma harzianum*

The enzymes derived from the genus *Stenotrophomonas*, the genus *Rhodococcus*, and the genus *Pimelobacter*, as listed above, have not been purified, and thus the properties of these enzymes still remain to be clarified. Although the enzyme derived from the genus *Arthrobacter* has been purified, its properties still remain unknown.

N-acyl-D-glutamic acid amidohydrolase derived from the genus *Pseudomonas*, and N-acyl-D-glutamic acid deacetylase, N-acyl-D-aspartic acid amide hydrolase, and D-aminoacylase derived from the genus *Alcaligenes* A-6 strain have been reported to be all inactive to N-acetyl-D-tryptophan.

According to references, the enzymes derived from the genus *Pseudomonas*, the genus *Streptomyces*, the genus *Trichoderma*, and the genus *Amycolatopsis* showed as low as 10 U/mg or lower of activity to N-acetyl-D-tryptophan and no activity to N-acetyl-D-tryptophan.

Furthermore, the activities of the enzymes derived from another strain DA1 belonging to the genus *Alcaligenes*, from the genus *Hypomyces*, and from the genus *Sebekia* are 100 U/mg or lower. On the other hand, the activity of the enzyme derived from another strain DA181 of the genus *Alcaligenes* has been reported to be as high as about 600 U/mg for N-acetyl-D-tryptophan. However, its stereoselectivity is not strict because this enzyme also shows the activity of about 11 U/mg to N-acetyl-L-tryptophan.

A novel D-aminoacylase derived from *Alcaligenes* sp. (WO00/23598) has been reported to act on N-acetyl-D-tryptophan. However the report shows only that the enzyme has the hydrolytic activity to 25 mM N-acetyl-DL-tryptophan and 10 mM N-acetyl-D-tryptophan. This D-aminoacylase is reportedly a novel enzyme capable of catalyzing the hydrolysis of 10 g/l N-acetyl-D-tryptophan.

On the other hand, the known D-aminoacylase derived from *Alcaligenes denitrificans* subsp. *xylosoxydans* MI-4 strain was found to be able to produce about 2.5 g/l D-tryptophan from the substrate, 150 g/l N-acetyl-DL-tryptophan, which corresponds to 75 g/l N-acetyl-D-tryptophan, as shown in FIG. 1. Thus, the enzyme was confirmed to have a sufficiently high activity to hydrolyze such a high concentration of the substrate.

It has been reported that the D-aminoacylases derived from *Methylobacterium mesophilicum* and *Nocardioides thermolilacinus* act on N-acetyl-D-tryptophan, and the catalytic reaction are hardly inhibited by the substrate even at concentrations as high as 100 g/l. However, the report does not mention the competitive inhibition by N-acetyl-L-tryptophan for the two enzymes. In addition, no detailed information is available for the two enzymes, and particularly, the enzyme derived from *Nocardioides thermolilacinus* has been neither purified nor characterized so far.

It was reported that when *E. coli* transformed with DNA containing a D-aminoacylase gene derived from *Methylobacterium mesophilicum* was incubated with 100 g/l N-acetyl-DL-tryptophan, D-tryptophan was produced in yield of about 90% from the substrate, N-acetyl-D-tryptophan (WO02/061077). However, there is no report on the production of D-tryptophan from higher concentrations of the substrate. For industrial production of D-tryptophan, it is desirable to hydrolyze a high concentration of the substrate, N-acetyl-DL-tryptophan, into D-tryptophan.

SUMMARY OF THE INVENTION

An objective of the present invention is to provide mutant D-aminoacylases that ensure the stereoselective production of a high concentration of D-tryptophan using a high concentration of N-acetyl-DL-tryptophan as a substrate. Another objective of the present invention is to provide genes encoding the enzymes. Still another objective of the present invention is to provide methods for producing D-amino acids using the mutant D-aminoacylases and the genes encoding thereof.

The present inventors focused on the fact that the D-aminoacylase derived from *Alcaligenes denitrificans* subsp. *xylosoxydans* MI-4 strain has an exceedingly high specific activity (404 U/mg) to N-acetyl-D-methionine. According to references, the D-aminoacylase had only 20 U/mg or lower activity to N-acetyl-D-tryptophan. The present inventors cloned the gene encoding the enzyme into *E. coli*, purified the cloned enzyme, and measured its specific activity. Contrary to the reported values, the enzyme had an exceedingly high specific activity (528 U/mg) to N-acetyl-D-tryptophan. In addition, the enzyme was inactive to N-acetyl-L-tryptophan. Thus, this enzyme can be useful to produce D-tryptophan from N-acetyl-DL-tryptophan.

The present inventors produced D-tryptophan by hydrolyzing N-acetyl-DL-tryptophan using the D-aminoacylase, and then found that the amount of D-tryptophan produced decreased when the substrate concentration exceeded a threshold. The present inventors sought the reason why the amount of D-tryptophan produced was decreased. As a result, the D-aminoacylase was inhibited strongly by a higher concentration of the substrate, N-acetyl-D-tryptophan or N-acetyl-L-tryptophan, than a threshold.

The industrial scale production of D-amino acids requires the use of an enzyme that produces D-amino acid at a concentration as high as possible. Such an enzyme should maintain its enzymatic activity at high substrate concentrations. Thus, for the production of D-tryptophan, it is desirable to provide a D-aminoacylase whose catalytic reaction is hard to be inhibited by N-acetyl-D-tryptophan.

Recent technical improvements in gene engineering have enabled modification of various natures of proteins to be more industrially useful by artificially modifying their amino acid sequences. The present inventors modified a D-aminoacylase gene derived from *Alcaligenes denitrificans* subsp. *xylosoxydans* MI-4 to achieve the objectives described above. The inventors then succeeded in obtaining mutant D-aminoacylases that ensure the production of a higher concentration of D-tryptophan from a higher concentration of N-acetyl-DL-tryptophan.

Furthermore, the present inventors found that D-amino acid could be produced efficiently by incubating the modified mutant D-aminoacylases with N-acyl-DL-amino acid under an appropriate condition. The mutant D-aminoacylases of the present invention, in particular, are less inhibited by N-acetyl-D-tryptophan than wild-type D-aminoacylase. This property revealed that, the mutants are suitably used to produce D-tryptophan at a high concentration and is thus industrially useful.

Specifically, the present invention relates to mutant D-aminoacylases and uses thereof as described below.

[1] a polypeptide having the activity of producing D-tryptophan in the presence of N-acetyl-D-tryptophan, which comprises:

(a) the amino acid sequence of SEQ ID NO: 1, in which an amino acid has been substituted for at least one amino acid residue selected from the group consisting of alanine at position 154, methionine at position 347, and arginine at position 374; or (b) the amino acid sequence of (a), in which one or more amino acids other than amino acid residues at 154, 347, and 374 have been substituted, deleted, added and/or inserted;

[2] the polypeptide according to [1], which comprises the amino acid sequence of SEQ ID NO: 1 which contains any one of amino acid substitutions selected from the group consisting of:

(A) substitution of alanine at position 154 with any one of amino acid selected from the group consisting of valine, cysteine, and threonine;

(B) substitution of methionine at position 347 with any one of amino acid selected from the group consisting of glycine, glutamine, serine, asparagine, alanine, isoleucine, and proline; and (C) substitution of arginine at position 374 with any one of amino acid selected from the group consisting of phenylalanine, lysine, leucine, tyrosine, histidine, isoleucine, and tryptophan;

[3] the polypeptide according to [1], which comprises the amino acid sequence of SEQ ID NO: 1 which contains amino acid substitutions of two or more amino acid residues selected from the group consisting of alanine at position 154, methionine at position 347, and arginine at position 374;

[4] the polypeptide according to [3], which comprises the amino acid sequence of SEQ ID NO: 1 which contains amino acid substitutions of alanine at position 154, methionine at position 347, and arginine at position 374;

[5] the polypeptide according to [1], which hydrolyzes specifically N-acetyl-D-tryptophan from 120 g/l N-acetyl-DL-tryptophan as a substrate and thus produces D-tryptophan in 80% or higher yield;

[6] the polypeptide according to [1], which has the activity of producing D-tryptophan in the presence of N-acetyl-D-tryptophan and N-acetyl-L-tryptophan;

[7] a polypeptide comprising the amino acid sequence of SEQ ID NO: 1 that contains any one of:

(1) mutation of alanine to valine at position 154 and mutation of methionine to alanine at position 347;

(2) mutation of methionine to alanine at position 347 and mutation of arginine to histidine at position 374;

(3) mutation of methionine to alanine at position 347 and mutation of arginine to phenylalanine at position 374;

(4) mutation of methionine to glutamine at position 347 and mutation of arginine to histidine at position 374;

(5) mutation of alanine to valine at position 154, mutation of methionine to alanine at position 347, and mutation of arginine to phenylalanine at position 374;

(6) mutation of alanine to valine at position 154, mutation of methionine to glutamine at position 347, and mutation of arginine to histidine at position 374;

(7) mutation of alanine to threonine at position 154, mutation of methionine to alanine at position 347, and mutation of arginine to histidine at position 374;

(8) mutation of alanine to threonine at position 154, mutation of methionine to alanine at position 347, and mutation of arginine to phenylalanine at position 374;

(9) mutation of alanine to threonine at position 154, mutation of methionine to glutamine at position 347, and mutation of arginine to histidine at position 374;

(10) mutation of alanine to threonine at a position 154, mutation of methionine to glutamine at position 347and mutation of arginine to phenylalanine at position 374;

[8] a polynucleotide encoding the polypeptide according to [1] or [7];

[9] the polynucleotide according to [8], which comprises the nucleotide sequence of SEQ ID NO: 3 that comprises nucleotide sequence substitutions selected from the group consisting of:

(a) substitution of the nucleotide sequence gcg at 460 to 462 with a nucleotide sequence selected from the group consisting of gta, tgc, and aca;

(b) substitution of the nucleotide sequence atg at 1039 to 1041 with a nucleotide sequence selected from the group consisting of ggt, caa, tct, aac, gca, ata, and ccc; and (c) substitution of the nucleotide sequence cgc at 1120 to 1122 with a nucleotide sequence selected from the group consisting of ttt, aaa, ctt, tat, cac, ata, and tgg;

[10] the polynucleotide according to [8], which comprises the nucleotide sequence of SEQ ID NO: 3 which contains nucleotide substitutions of two or more regions selected from the group consisting of the nucleotide sequence gcg at 460 to 462, the nucleotide sequence atg at 1039 to 1041, and the nucleotide sequence cgc at 1120 to 1122;

[11] the polynucleotide according to [10], which comprises the nucleotide sequence of SEQ ID NO: 3 which contains nucleotide substitution of the nucleotide sequence gcg at 460 to 462, the nucleotide sequence atg at 1039 to 1041, and the nucleotide sequence cgc at 1120 to 1122;

[12] a polynucleotide comprising the nucleotide sequence of SEQ ID NO: 3;

[13] a vector containing the polynucleotide according to [8] as an insert;

[14] a transformant containing the vector according to [13];

[15] the transformant according to [14], which is *E. coli* carrying the polynucleotide according to [9];

[16] a method for producing the polypeptide according to [1] or [7], which comprises culturing the transformant according to [14];

[17] a method for producing D-amino acid, which comprises the steps of contacting N-acyl-DL-amino acid with at least one enzymatically active material selected from-the group consisting of:

(a) the polypeptide according to [1] or [7];

(b) the transformant according to [14]; and (c) a processed product of the transformant according to (b); and recovering the produced D-amino acid;

[18] the production method according to [17], wherein N-acyl-DL-amino acid is N-acyl-DL-tryptophan;

[19] the production method according to [18], wherein N-acyl-DL-tryptophan is N-acetyl-DL-tryptophan;

[20] the production method according to [19], wherein the concentration of N-acetyl-DL-tryptophan is 120 g/l or higher;

[21] the polynucleotide according to [8], which comprises the nucleotide sequence of SEQ ID NO: 2 that comprises nucleotide sequence substitutions selected from the group consisting of:

(a) substitution of the nucleotide sequence gcg at 460 to 462 with a nucleotide sequence selected from the group consisting of gta, tgc, and aca;

(b) substitution of the nucleotide sequence atg at 1039 to 1041 with a nucleotide sequence selected from the group consisting of ggt, caa, tct, aac, gca, ata, and ccc; and (c) substitution of the nucleotide sequence cgc at 1120 to 1122 with a nucleotide sequence selected from the group consisting of ttt, aaa, ctt, tat, cac, ata, and tgg;

[22] the polynucleotide according to [8], which comprises the nucleotide sequence of SEQ ID NO: 2 which contains nucleotide substitutions of two or more regions selected from the group consisting of the nucleotide sequence gcg at 460 to 462, the nucleotide sequence atg at 1039 to 1041, and the nucleotide sequence cgc at 1120 to 1122;

[23] the polynucleotide according to [22], which comprises the nucleotide sequence of SEQ ID NO: 2 which contains nucleotide substitution of the nucleotide sequence gcg at 460 to 462, the nucleotide sequence atg at 1039 to 1041, and the nucleotide sequence cgc at 1120 to 1122.

DETAILED DESCRIPTION OF THE INVENTION

Figure 1:
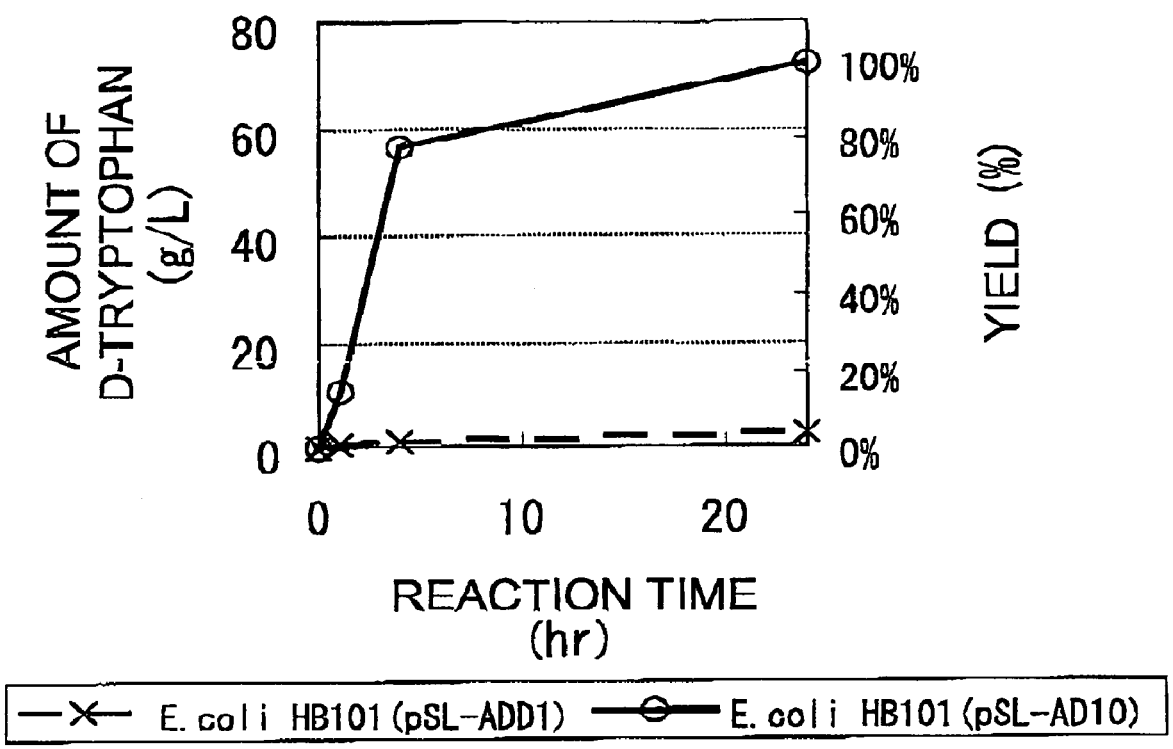
FIG. 1 shows production of D-tryptophan through the hydrolysis of 15% N-acetyl-DL-tryptophan using a culture medium of recombinant *E. coli* producing wild-type or mutant D-aminoacylase. The ordinate axis indicates the amount of D-tryptophan produced (g/l) or yield (%); the abscissa axis indicates the reaction time (h).

The present invention provides mutants of D-aminoacylases derived from *Alcaligenes denitrificans* subsp. *xylosoxydans* MI-4.

As used herein, the term "D-aminoacylase" refers to an enzyme that catalyzes the production of organic acids and D-amino acids from N-acyl-D-amino acids. The phrase "inhibition of D-aminoacylase" refers to substrate inhibition of N-acetyl-D-amino acids and/or competitive inhibition of N-acetyl-L-amino acids. In the present invention, D-aminoacylase activity can be determined by a method that is routinely used by those skilled in the art. For example, D-aminoacylase activity can be determined by the method described below.

The enzyme reaction can be achieved by incubating 1.0 ml of a reaction solution containing 20 mM N-acetyl-D-tryptophan (Sigma), 50 mM Tris-hydrochloride buffer (pH 7.5), and an enzyme solution at 30° C. for 10 minutes. Then, the reaction is stopped by adding 0.5 ml of a stop solution containing TCA (comprising 0.11 M trichloroacetic acid, 0.22 M sodium acetate, and 0.33 M acetic acid). The amount of D-tryptophan produced can be determined by TNBS method (Biosci. Biotech. Biochem., 58, 24 (1994)).

For example, 0.25 ml of 100 mM $Na_2B_4O_7$ is added to 0.25 ml of the stop solution, 10 µl of 110 mM TNBS (trinitrobenzenesulfonic acid) solution is added to the mixed solution, and immediately thereafter, the resulting mixture is stirred. After the mixture is allowed to stand for five minutes, 1 ml of 100 mM $NaHPO_4$ containing 1.5 mM $Na_2SO_3$ is added to the mixture to stop the color reaction. Then, the absorbance of the solution is determined at 420 nm. One unit of the enzyme activity is defined as the amount of enzyme that catalyzes the production of 1 µmol of D-tryptophan at 30° C. for one minute.

In the present invention, D-tryptophan produced by the enzyme reaction or the reaction using microbial cells can be quantified by high-performance liquid chromatography using an ODS column (column: Wakosil II 5C18 ($\phi$ 4.6×250 mm); Wako Pure Chemical Industries; elution buffer, $CH_3CN$/50 mM $KH_2PO_4 \cdot H_3PO_4$ (pH 2.5)=2:8; detection wavelength, A280 nm; flow rate, 1.0 mL/min; column temperature, 40° C.). The retention time was 3.8 minutes for D-tryptophan, and 10.7 minutes for N-acetyl-DL-tryptophan. Protein amounts were determined using Bio-Rad Protein Assay Kit (Bio-Rad). The standard protein used was bovine plasma albumin.

Herein, modification of an amino acid residue in an amino acid sequence is represented according to the following rule. An amino acid position is numbered by taking the N terminal residue of SEQ ID NO: 1 as 1. The one-letter code for a wild-type amino acid residue, the number of position, and the one-letter code for a substitute amino acid residue is arranged in this order from the left. For example, the substitution of Ala at position 154 with an amino acid X is represented by A154X. Likewise, the substitution of Met at position 347 with an amino acid Y is represented by M347Y, and the substitution of Arg at position 374 with an amino acid Z is represented by R374Z. A154X/M347Y/R374Z represents that these three modifications occur simultaneously.

The amino acid sequence of D-aminoacylase derived from *Alcaligenes denitrificans* subsp. *xylosoxydans* MI-4 is shown by SEQ ID NO: 1. Mutant D-aminoacylases of the present invention has the amino acid sequence of SEQ ID NO: 1, in which at least one amino acid residue selected from the group consisting of alanine at position 154, methionine at position 347, and arginine at position 374 is replaced with another amino acid. A mutant enzyme of the present invention can be prepared by amino acid substitution of at least one of the three amino acid, for example, any one or two of the three amino acid residues, or all the three residues.

The substitute amino acid residue at position 154 is preferably valine, cysteine, or threonine, and more preferably valine. The substitute residue at position 347 is preferably glycine, glutamine, serine, asparagine, alanine, isoleucine, or proline, and more preferably alanine. The substitute residue at position 374 is preferably, phenylalanine, lysine, leucine, tyrosine, histidine, isoleucine, or tryptophan, and more preferably phenylalanine.

The present invention provides a polypeptide comprising the amino acid sequence of SEQ ID NO: 1, in which at least one amino acid residue selected from the group consisting of alanine at position 154, methionine at position 347, and arginine at position 374 is replaced with another amino acid. The polypeptide of the present invention has D-aminoacylase activity and is less inhibited by the substrate N-acetyl-D-tryptophan than the wild-type D-aminoacylase derived from *Alcaligenes denitrificans* subsp. *xylosoxydans* MI-4. Hereinafter, *Alcaligenes denitrificans* subsp. *xylosoxydans* MI-drived D-aminoacylase is sometimes referred to as "wild-type D-aminoacylase". One embodiment of the present invention is a polypeptide, which is more resistant to the competitive inhibition by N-acetyl-L-tryptophan as well as the substrate inhibition described above as compared with the wild-type D-amionoacylase.

A preferred amino acid sequence of the polypeptide of the present invention is a modified amino acid sequence derived from the sequence of SEQ ID NO: 1, in which alanine at position 154, methionine at position 347, and arginine at position 374 have been substituted as shown in Table 1. These mutated polypeptides are preferred because they are resistant to both of substrate inhibition and competitive inhibition as described above.

TABLE 1

| Amino acid 154 alanine | Amino acid 347 methionine | Amino acid 374 arginine |
|---|---|---|
| (1) valine | alanine | — |
| (2) — | alanine | histidine |
| (3) — | alanine | phenylalanine |
| (4) — | glutamine | histidine |
| (5) valine | alanine | phenylalanine |
| (6) valine | glutamine | histidine |
| (7) threonine | alanine | histidine |
| (8) threonine | alanine | phenylalanine |
| (9) threonine | glutamine | histidine |
| (10) threonine | glutamine | phenylalanine |

—: no substitution

A mutant of the present invention may contain additional mutations including one or more amino acid substitutions, deletions, additions and/or insertions as well as the above-described mutations, as long as it contains the above-mentioned mutations in its amino acid sequence and it is more resistant to the inhibition by N-acetyl-D-tryptophan and/or N-acetyl-L-tryptophan compared to the wild-type enzyme. Such mutations can artificially be introduced or can be generated spontaneously. Mutants of the present invention include both of artificial or spontaneous mutants. The number of mutated amino acids in mutants of the present invention are typically 50 amino acids or less, preferably 30 amino acids or less, and more preferably 10 amino acids or less (for example, 5 amino acids or less, 3 amino acids or less).

When mutants of the present invention have mutations such as amino acid deletions, additions, or insertions at positions other than position 154, 347, or 374, these amino acid positions counted from the N-terminus can be altered. In such cases, an altered amino acid sequence of SEQ ID NO: 1 can be converted into a mutant of the present invention by replacing amino acid residues at positions corresponding to 154, 347, and 374 with different amino acids. In other words, the polypeptides of the present invention includes polypeptides (1) comprising the amino acid sequence of SEQ ID NO: 1, in which at least one amino acid selected from the group consisting of amino acids corresponding to Ala at 154, Met at 347, and Arg at 374 has been replaced with another amino acid, and (2) having a reduced tendency to be inhibited by N-acetyl-D-tryptophan and/or N-acetyl-L-tryptophan. :

Such a corresponding position can be found by aligning an amino acid sequence around the mutated position of an altered amino acid sequence with an amino acid sequence around the mutant position in SEQ ID NO: 1. This operation is called aligning of amino acid sequences. An algorithm for such an alignment is, for example, BLAST. Those skilled in the art can find corresponding amino acid positions in amino acid sequences with different lengths based on the alignment. Thus, a polypeptide that comprises an amino acid sequence containing, for example, the substituted amino acid residues listed in Table 1 at the corresponding positions identified as described above is a preferred mutant of the present invention.

In the present invention, an amino acid sequence that contains extra mutations in addition to alanine at position 154, methionine at position 347, and arginine at position 374 preferably retains high homology to the amino acid sequence of SEQ ID NO: 1. The term "high homology" refers to, for example, 80% or higher, preferably 85% or higher, more preferably 90% or higher, still more preferably 95% or higher homology.

Such additional mutations referred to in the present invention are preferably conservative substitutions. In general, a substitute amino acid preferably has similar properties to an amino acid to be substituted so as to maintain the protein function. Such amino acid substitution is called conservative substitution.

For example, Ala, Val, Leu, Ile, Pro, Met, Phe, and Trp are categorized into non-polar amino acids and have similar properties to each other. Non-charged amino acids include Gly, Ser, Thr, Cys, Tyr, Asn, and Gln. Acidic amino acids include Asp and Glu. Basic amino acids include Lys, Arg, and His.

Polypeptides of the present invention is characterized by its improved resistance to the substrate inhibition by N-acetyl-D-tryptophan and/or competitive inhibition by N-acetyl-L-tryptophan as compared with wild-type D-aminoacylase derived from *Alcaligenes denitrificans* subsp. *xylosoxydans* MI-4. Compounds, substrate inhibition or competitive inhibition by which is to be impaired, are not restricted to these compounds. Specifically, the substrate inhibition or competitive inhibition caused by compounds other than these compounds may be impaired additionally, as long as polypeptides of the present invention resist the substrate inhibition by N-acetyl-D-tryptophan and/or competitive inhibition by N-acetyl-L-tryptophan. Besides the resistance to the substrate inhibition and competitive inhibition, a mutant of this invention can contain an additional phenotype introduced through another gene modification.

Polypeptides of the present invention can produce D-tryptophan in 80% or higher yield from 12% or higher concentration of N-acetyl-DL-tryptophan. A preferred polypeptide of the present invention is capable of producing D-tryptophan in 80% or higher yield from 15% or higher or 17% concentration of N-acetyl-DL-tryptophan.

In addition, a preferred polypeptide of the present invention is capable of producing D-tryptophan in 50% or higher yield from 20% or higher concentration of N-acetyl-DL-tryptophan. A more preferred polypeptide is capable of producing D-tryptophan in 50% or higher yield from 22% or higher concentration of N-acetyl-DL-tryptophan.

The 80% or higher yield or at 50% or higher yield as described above means that the yield of D-tryptophan obtained from the substrate N-acetyl-D-tryptophan in a reaction solution including 10 U/mL enzyme at pH 8.0 at 30° C.

Wild-type or mutant D-aminoacylase extract can be obtained by, for example, recovering microbial cells by filtration and centrifugation, suspending them in a buffer, and disrupting them using a Bead-Beater (BIOSPEC PRODUCT). Reaction solutions containing 10 U/mL enzyme thus obtained 300 mM Tris-hydrochloride buffer (pH 8.0), and 12%, 15%, 17%, 20% or 22% N-acetyl-DL-tryptophan, are incubated at 30° C. for 24 hours while being shaken. Thus, D-tryptophan can be produced in 80% or higher yield from 12%, 15%, or 17% substrate, or in 50% or higher yield from 20% or 22% substrate.

The present invention also relates to polynucleotides encoding polypeptides of the present invention. A nucleotide sequence encoding the amino acid sequence of SEQ ID NO: 1 is shown by SEQ ID NO:. 2. Polynucleotides of the present invention include a DNA that comprises a nucleotide sequence encoding the amino acid sequence of SEQ ID NO: 1, in which the codons for amino acids corresponding to alanine at position 154, methionine at position 347, and arginine at position 374 have been replaced with the codons for substitute amino acid residues. A nucleotide sequence encoding an amino acid sequence can be designed by selecting codons corresponding to respective amino acids in accordance with the genetic code system. It is well known that an amino acid is encoded by not a single but multiple codons because of codon degeneracy. Thus, nucleotide sequences encoding the amino acid sequence of SEQ ID NO: 1 include not only the nucleotide sequence of SEQ ID NO: 2 but also all nucleotide sequences designed with synonymous codons.

The present invention provides D-aminoacylase expression vectors prepared by inserting a polynucleotide encoding a D-aminoacylase of the present invention, which is obtained as described above into a known expression vector. D-aminoacylase of the present invention can be obtained as a recombinant polypeptide by culturing a transformant which has been transformed with an expression vector as described above.

Polypeptides of the present invention can be prepared as described below. For example, a gene encoding a polypeptide of the present invention can be prepared from the wild-type D-aminoacylase gene by introducing mutations at desired amino acid positions. The nucleotide sequence of the D-aminoacylase gene derived from wild-type *Alcaligenes denitrificans* subsp. *xylosoxydans* MI-4 is shown by SEQ ID NO: 2.

A polynucleotide of the present invention is useful in producing a polypeptide of the present invention. A polypeptide comprising an amino acid sequence of interest can be obtained as a recombinant polypeptide by expressing a polynucleotide of the present invention in an appropriate host. Polypeptides of this invention may be modified in various ways to improve the productivity when expressed in a host. For example, codons corresponding to rare codons in a host are removed from the polynucleotides, or the polynucleotides are modified for the compatibility of codon usage and GC content with a host. The nucleotide sequences can be modified without altering the amino acid sequences encoded by the polynucleotides by converting the original codon to an alternative codon for the same amino acid based on the degeneracy of genetic code.

For example, the nucleotide sequences of the polynucleotides may be modified to increase the productivity of D-aminoacylase in *E. coli* or to improve the stability of the D-aminoacylase gene in *E. coli*. Specifically, codons corresponding to rare codons in *E. coli* can be removed from the polynucleotides, and the polynucleotides can be modified for the compatibility of codon usage and GC content with *E. coli*. The nucleotide sequence that comprises a nucleotide sequence encoding a mutant of the present invention, which has been modified to be suitable for expression in *E. coli*, is shown by SEQ ID NO: 3. The nucleotide sequence of SEQ ID NO: 3 encodes the amino acid sequence of SEQ ID NO: 1.

Thus, a DNA that is suitable for expressing a mutant of the present invention in *E. coli* can be prepared using a DNA encoding a mutant of the present invention designed by modifying the nucleotide sequence of SEQ ID NO: 3. The following nucleotide sequences are examples of nucleotide sequences encoding preferred substitute amino acid residues at position 154, at position 347, and at position 374 according to the present invention. Preferred polynucleotides of the present invention include DNAs that comprise the nucleotide sequence of SEQ ID NO: 3 in which the nucleotide sequence listed below has been substituted for at least one region selected from the group consisting of nucleotides 460 to 462, 1039 to 1041, and 1120 to 1122.

| | |
|---|---|
| Position 154: (Ala/460-gcg) | valine/gta |
| | cysteine/tgc |
| | threonine/aca |
| Position 347: (Met/1039-atg) | glycine/ggt |
| | glutamine/caa |
| | serine/tct |
| | asparagine/aac |
| | alanine/gca |
| | isoleucine/ata |
| | proline/ccc |
| Position 374: (Arg/1120-cgc) | phenylalanine/ttt |
| | lysine/aaa |
| | leucine/ctt |
| | tyrosine/tat |
| | histidine/cac |
| | isoleucine/ata |
| | tryptophan/tgg |

The plasmid pSL-ADD6 containing a DNA comprising the nucleotide sequence of SEQ ID NO: 3 has been deposited under the following conditions. The DNA inserted into the plasmid can be used preferably in producing mutants of the present invention in *E. coli*.

Name and Address of Depositary Institution
Name: International Patent Organism Depositary, National Institute of Advanced Industrial Science and Technology (AIST), Independent Administrative Institution
(Previous Name: The National Institute of Bioscience and Human-Technology, The Agency of Industrial Science and Technology, The Ministry of International Trade and Industry)
Address: AIST Tsukuba Central 6, 1-1-3 Higashi, Tsukuba, Ibaraki, 305-8566, Japan (Post code: 305-8566)
Date of Deposition: Oct. 17, 2003 (original deposit was made on Nov. 12, 2002)
Accession Number: FERM BP-08508

Mutant D-aminoacylases can be obtained by introducing mutations into the wild-type gene using a known technique of mutagenesis that has been used routinely by those skilled in the art, such as site-directed mutagenesis and random mutagenesis. Such techniques of mutagenesis include, for example, error-prone PCR, site-directed saturation mutagenesis, cassette mutagenesis, DNA shuffling, and StEP (Appl. Microbiol. Biotechnol., 55, 519, 2001). For example, using as a template a DNA of interest into which mutations are to be introduced, mutations can be introduced at random into the DNA by allowing the DNA to replicate using a low-fidelity PCR method (error-prone PCR) in which the fidelity of nucleotide incorporation by Taq DNA polymerase has been impaired.

Specifically, error-prone PCR in which the fidelity of nucleotide incorporation by Taq DNA polymerase has been impaired can be performed by: (1) increasing $MgCl_2$ concentration in the PCR reaction solution; (2) adding $MnCl_2$ to the reaction solution; (3) using unequal concentrations of the four types of nucleotides in the reaction solution; (4) adding nucleotide analogs to the reaction solution. Alternatively, when using a template DNA that readily undergoes nucleotide substitution, such as a DNA having high GC content, random mutations can be introduced, without the procedure described above, by using a Taq DNA polymerase with which the fidelity of nucleotide incorporation is relatively low.

A library of mutants can be prepared by inserting the replicated DNA fragment into a known expression vector and preparing transformants resulting from transformation with the expression vector. A desired mutant whose competitive inhibition by N-acetyl-L-tryptophan and/or substrate inhibition by N-acetyl-D-tryptophan have been reduced can be isolated, for example, by contacting the mutant with a N-acetyl-DL-tryptophan mixture as the substrate, in which the proportion of N-acetyl-L-tryptophan has been increased, and comparing the amounts of D-tryptophan produced between the mutant and wild type.

For example, a culture medium of a transformant is incubated with a mixture of 5% N-acetyl-DL-tryptophan and 1% N-acetyl-L-tryptophan as the substrate, and then a mutant with which the amount of D-tryptophan produced in the reaction solution is larger than that with the wild type may be selected as a mutant whose competitive inhibition by N-acetyl-L-tryptophan and/or substrate inhibition by N-acetyl-D-tryptophan have been reduced.

Once mutated sites (sites of amino acid substitution) that give desired effects are identified in such experiments using random mutagenesis, then, as a next step, site-specific and random amino acid substitutions can be achieved by using the method described below to select the most suitable amino acid substitutions. For example, if NNN (N is a mixture of A, T, G, and C) denotes a codon corresponding to a site to which an amino acid substitution is to be introduced, a mixture of 64 types of primers covering the site of NNN is designed and synthesized. Another primer that contains a nucleotide sequence corresponding to that of wild-type DNA at an appropriate position is synthesized, so as to be paired with the one described above. Preferably, each primer is designed to have a recognition site, such as a restriction enzyme site, at the 5' end. With this pair of primers, a library that contains DNA fragments encoding all codon types for the naturally-occurring amino acids at specific sites can be prepared by PCR using the wild-type DNA as a template.

Both ends of the amplified DNA fragment are digested with appropriate restriction enzymes or such. The fragment is ligated with an expression vector containing the wild-type DNA treated with the same procedure. Transformants are prepared through transformation with an expression vector described above. Thus, a library of transformants each expressing the enzyme in which an amino acid at a specific site has been replaced with another naturally-occurring amino acid can be prepared. An amino acid substitution which is the most effective to reduce the degree of competitive inhibition by N-acetyl-L-tryptophan and/or substrate inhibition by N-acetyl-D-tryptophan can be selected by using an N-acetyl-DL-tryptophan mixture as the substrate, in which the proportion of N-acetyl-L-tryptophan has been increased, and selecting a mutant that produces D-tryptophan at a higher level.

For example, a culture medium of a transformant is incubated with a mixture of 5% N-acetyl-DL-tryptophan and 2% N-acetyl-L-tryptophan as the substrate, and then a mutant with which the amount of D-tryptophan produced in the reaction solution is larger than that with the wild type may be selected as a mutant containing amino acid residues that are the most suitable to reduce the degree of competitive inhibition by N-acetyl-L-tryptophan and/or substrate inhibition by N-acetyl-D-tryptophan. Once two or more preferred sites of amino acid substitutions and preferred amino acid residues substituted are identified, a mutant in which a property of interest has been further improved can be obtained by combining the amino acid substitutions on purpose or at random. For example, when amino acid substitutions at three amino acid sites are intended to be combined at random, plasmids each of which the gene for one of the three mutant enzymes is digested at three appropriate sites with restriction enzymes or such and then DNA fragments covering the sites for the amino acid substitutions are purified and recovered.

All the DNAs treated are combined to cover the full length of the mutant enzyme gene. A plasmid library of mutants that comprises -all possible combinations of amino acid substitutions at the three sites can be prepared by ligating the mixture at random using T4 DNA ligase. By using a DNA fragment derived from the wild type at one of the three amino acid substitution sites, a plasmid library that also contains mutants containing two amino acid substitutions, and mutants containing single amino acid substitution can be prepared at the same time. Thus, a library of transformants that express mutant enzymes containing one to three amino acid substitutions can be obtained by preparing transformants through transformation with the plasmid library.

An optimal combination of amino acid substitutions which are effective to reduce the degree of competitive inhibition by N-acetyl-L-tryptophan and/or substrate inhibition by N-acetyl-D-tryptophan can be selected by using as the substrate a mixture of N-acetyl-DL-tryptophan, in which the proportion of N-acetyl-L-tryptophan has been increased, and selecting a mutant that produces D-tryptophan at a higher level.

For example, a culture medium of a transformant is incubated with a mixture of 2% N-acetyl-DL-tryptophan and 3.5% N-acetyl-L-tryptophan as the substrate, and then a mutant with which the amount of D-tryptophan produced in the reaction solution is larger than that with the wild type may be selected as a mutant containing a combination of amino acid substitutions that is the most suitable to reduce the degree of competitive inhibition by N-acetyl-L-tryptophan and/or substrate inhibition by N-acetyl-D-tryptophan.

There is no particular limitation on the type of microorganism to be transformed for expression of D-aminoacylases of the present invention, as long as such a microorganism is capable of being transformed with a recombinant vector containing a polynucleotide encoding a D-aminoacylase of this invention and capable of expressing it. The present invention encompasses such a transformant and methods for producing a D-aminoacylase of the present invention, which comprise culturing the transformant. Available microorganisms as host to prepare the transformant include, for example, the following microorganisms:

Bacteria for which host-vector systems are developed:
- the genus *Escherichia*,
- the genus *Bacillus*,
- the genus *Pseudomonas*,
- the genus *Serratia*,
- the genus *Brevibacterium*,
- the genus *Corynebacterium*,
- the genus *Streptococcus*, or
- the genus *Lactobacillus*.

Actinomycetes for which host-vector systems are developed:
- the genus *Rhodococcus* or
- the genus *Streptomyces*.

Yeast for which host-vector systems are developed:
- the genus *Saccharomyces*,
- the genus *Kluyveromyces*,
- the genus *Schizosaccharomyces*,
- the genus *Zygosaccharomyces*,
- the genus *Yarrowia*,
- the genus *Trichosporon*,
- the genus *Rhodosporidium*,
- the genus *Pichia*, or
- the genus *Candida*.

Fungi for which host-vector systems are developed:
- the genus *Neurospora*,
- the genus *Aspergillus*,
- the genus *Cephalosporium*, or
- the genus *Trichoderma*.

The procedure for generating transformants and constructing recombinant vectors suitable for hosts can be performed according to standard techniques known in the fields of molecular biology, bioengineering, and genetic engineering (for example, Sambrook et al., Molecular Cloning, Cold Spring Harbor Laboratories).

To express a D-aminoacylase mutant gene or D-aminoacylase modified gene of the present invention in microbial cells and such, first, a polynucleotide of the present invention is inserted into a plasmid vector or a phase vector stably existing in the microorganisms, and the genetic information is transcribed and translated. A promoter, which regulates transcription and translation, is inserted 5'-upstream of the polynucleotide of the present invention; preferably, a terminator is also inserted 3'-downstream of the polynucleotide. The promoter and terminator should function in microorganisms to be used as host cells. Vectors, promoters, and terminators functioning in various microorganisms are described in, for example, "Biseibutsugaku Kisokouza (Basic Course of Microbiology) Vol. 8 Idenshikougaku (Genetic Engineering), Kyoritsu Shuppan Co., Ltd., particularly for yeast, described in "Adv. Biochem. Eng. 43, 75-102 (1990), Yeast 8, 423-488 (1992)" etc.

For example, plasmid vectors such as pBR and pUC series, and promoters such as those of β-galactosidase (lac), tryptophan operon (trp), tac, trc (fusion of lac and trp), and those derived from λ-phage PL, PR, etc. can be used for the genus *Escherichia*, particularly *Escherichia coli*. Terminators derived from trpA, phage, and rrnB ribosomal RNA can also be used.

Vectors such as the pUB110 and pC194 series can be used for the genus *Bacillus* and can be integrated into chromosomes. Promoters and terminators such as those of alkaline protease (apr), neutral protease (npr), and amy (α-amylase) can be used.

Host-vector systems for the genus *Pseudomonas*, specifically *Pseudomonas putida* and *Pseudomonas cepacia*, have been developed. A broad host range vector pKT240 (containing genes necessary for autonomous replication derived from RSF1010) based on plasmid TOL that is involved in degradation of toluene compounds can be utilized. A promoter and terminator of a lipase (JP-A Hei 5-284973) gene and the like can be used.

Plasmid vectors such as pAJ43 (Gene 39, 281 (1985)) can be used for the genus *Brevibacterium*, especially *Brevibacterium lactofermentum*. Promoters and terminators for the genus *Escherichia* can be used for this microorganism.

Plasmid vectors such as pCS11 (JP-A Sho 57-183799) and pCB101 (Mol. Gen. Genet. 196, 175 (1984)) can be used for the genus *Corynebacterium*, particularly, *Corynebacterium glutamicum*.

Plasmid vectors such as pHV1301 (FEMS Microbiol. Lett., 26, 239 (1985)) and pGK1 (Appl. Environ. Microbiol.50, 94 (1985)) can be used for the genus *Streptococcus*.

For the genus *Lactobacillus*, pAM.β1 developed for the genus *Streptococcus* (J. Bacteriol. 137, 614 (1979)) can be used, and some of the promoters for the genus *Escherichia* are applicable.

For the genus *Rhodococcus*, a plasmid vector isolated from *Rhodococcus rhodochrous* and such can be used (J. Gen. Microbiol. 138, 1003 (1992)).

Plasmids functioning in the genus *Streptomyces* can be constructed by the method described in "Genetic Manipulation of Streptomyces: A Laboratory Manual Cold Spring Harbor Laboratories by Hopwood et al. (1985)." For example, pIJ486 (Mol. Gen. Genet. 203, 468-478 (1986)), pKC1064 (Gene 103, 97-99 (1991)), and PUWL-KS (Gene 165, 149-150 (1995)) can be used, particularly for *Streptomyces lividans*. Such plasmids can also be used for *Streptomyces virginiae* (Actinomycetol. 11, 46-53 (1997)).

Plasmids such as the YRp, YEp, YCp, and YIp series can be used for the genus *Saccharomyces*, especially for *Saccharomyces cerevisiae*. Integration vectors (such as EP 537456) using homologous recombination with multiple copies of a ribosomal DNA in genomic DNA are extremely useful because they are capable of introducing multiple copies of genes into the host genome and stably maintaining the genes. Furthermore, promoters and terminators of alcohol dehydrogenase (ADH), glyceraldehyde-3-phosphate dehydrogenase (GAPDH), acid phosphatase (PHO), β-galactosidase (GAL), phosphoglycerate kinase (PGK), enolase (ENO), etc. can be used.

Plasmids such as the series of 2 μm plasmids derived from *Saccharomyces cerevisiae*, the series of pKD1 plasmids (J. Bacteriol. 145, 382-390 (1981)), plasmids derived from pGK11 involved in killer activity, the series of KARS plasmids containing an autonomous replication gene from the genus *Kluyveromyces*, and vector plasmids (such as EP 537456) capable of being integrated into chromosomes by homologous recombination with ribosomal DNA can be used for the genus *Kluyveromyces*, particularly for *Kluyveromyces lactis*. Promoters and terminators derived from ADH and PGK are applicable.

For the genus *Schizosaccharomyces*, plasmid vectors containing ARS (a gene involved in autonomous replication) derived from Schizosaccharomyces pombe and containing selective markers supplementing auxotrophy of *Saccharomyces cerevisiae* can be used (Mol. Cell. Biol. 6, 80 (1986)). Furthermore, ADH promoter derived from *Schizosaccharomyces pombe* is applicable (EMBO J. 6, 729 (1987)). In particular, pAUR224 is commercially available from Takara Shuzo.

For the genus *Zygosaccharomyces*, plasmid vectors such as pSB3 (Nucleic Acids Res. 13, 4267 (1985)) derived from

*Zygosaccharomyces rouxii* can be used. Promoters of PHO5 derived from *Saccharomyces cerevisiae* and glycerolaldehyde-3-phosphate dehydrogenase (GAP-Zr) derived from *Zygosaccharomyces rouxii* (Agri. Biol. Chem. 54, 2521 (1990)), etc. are available.

A host-vector system has been developed for *Pichia angusta* (previous name: *Hansenula polymorpha*) among the genus *Pichia*. Usable vectors include *Pichia angusta*-derived genes (HARS1 and HARS2) involved in autonomous replication, but they are relatively unstable. Therefore, multi-copy integration of the gene into a chromosome is effective (Yeast 7, 431-443 (1991)). Promoters of AOX (alcohol oxidase) and FDH (formate dehydrogenase), which are induced by methanol and such, are also available. Host-vector systems for *Pichia pastoris* have been developed using genes such as PARS1 and PARS2 involved in autonomous replication derived from *Pichia* (Mol. Cell. Biol. 5, 3376 (1985)). Promoters such as a promoter of AOX with strong promoter activity induced by high-density culture and methanol are applicable (Nucleic Acids Res. 15, 3859 (1987)).

For the genus *Candida*, host-vector systems have been developed for *Candida maltosa, Candida albicans, Candida tropicalis, Candida utilis*, etc. Vectors for *Candida maltosa* using ARS, which was cloned from this strain, have been developed (Agri. Biol. Chem. 51, 51, 1587 (1987). Strong promoters for vectors that are able to be integrated into chromosomes have been developed for *Candida utilis* (JP-A Hei 08-173170).

In the genus *Aspergillus, Aspergillus niger* and *Aspergillus oryzae* have been most extensively studied. Plasmids able to be integrated into chromosomes are available. Promoters derived from extracellular protease and amylase are available (Trends in Biotechnology 7, 283-287 (1989)).

For the genus *Trichoderma*, host-vector systems based on *Trichoderma reesei* have been developed., and promoters derived from extracellular cellulase genes are available (Biotechnology 7, 596-603 (1989)).

Various host-vector systems for plants and animals, in addition to microorganisms, have been developed. In particular, expression systems for producing a large amount of foreign polypeptides in insects, particularly silkworms (Nature 315, 592-594 (1985)), and plants such as rapeseeds, corns, and potatoes have been developed and are available.

A D-aminoacylase of the present invention is prepared from a culture of microbial cells transformed with a recombinant vector containing a polynucleotide encoding the enzyme according to a conventional culturing method. Both synthetic medium and natural medium can be used, as long as they contain appropriate amounts of carbon source, nitrogen source, inorganic materials, and other nutrients. The medium may be liquid or solid.

Specifically, one, or two or more carbon sources are used, which are appropriately selected from carbon sources routinely used, including: sugars, such as glucose, fructose, maltose, galactose, starch, starch hydrolysate, molasses, and blackstrap molasses; naturally occurring carbohydrates, such as wheat and corn; alcohols, such as glycerol, methanol, and ethanol; fatty acids, such as acetic acid, gluconic acid, pyruvic acid, and citric acid; hydrocarbons, such as normal paraffin; amino acids, such as glycine, glutamine, and asparagine. One or two or more nitrogen sources are used, which are appropriately selected from organic nitrogen compounds, such as meat extract, peptone, yeast extract, soy bean hydrolysate, milk casein, casamino acid, various amino acids, corn steep liquor, other hydrolysates of animals, plants, microorganisms, and such; and inorganic nitrogen compounds, such as ammonium salts, such as ammonia, ammonium nitrate, ammonium sulfate, and ammonium chloride; nitrates, such as sodium nitrate; and urea.

Furthermore, small amounts of one or two or more inorganic salts are used, which are appropriately selected from phosphate, hydrochloride, nitrate, acetate, and others., of magnesium, manganese, potassium, calcium, sodium, copper, zinc, and others. If required, an anti-foaming agent can be used, which includes vegetable oil, detergent, and silicon.

The cells can be cultured in a culture medium solution containing the components described above by a typical culture method, such as shaking culture, aeration sinner culture, continuous culture, and feeding culture.

There is no limitation on the culture condition, as long as the strain of microorganism can be grown and produce D-aminoacylase. Such a culture condition is appropriately selected considering culture type, culture method, and others. Typically, it is preferable to culture at a temperature of 15 to 50° C., preferably at 25 to 35° C., after the pH at the start of culture is adjusted at 4 to 10, preferably 6 to 8.

After microbial cells are grown sufficiently, or during cell growth, the transformants are placed under a condition that allows inducing expression of a foreign gene. For example, the expression of a foreign gene placed downstream of the lac promoter is induced by adding IPTG. Alternatively, when a temperature-sensitive promoter is used, the cells are cultured at a temperature that enables to express the gene.

There is no limitation on the duration of culturing, as long as the culturing yields microbial cells having sufficiently high D-aminoacylase activity. Typical culturing period ranges from one day to 14 days, preferably one day to three days. A D-aminoacylase of the present invention produced and accumulated through gene expression can be collected and recovered by the procedures described below.

If D-aminoacylase accumulates in microbial cells, after culturing, the cells are collected by a method, such as filtration and centrifugation. The cells are washed with a buffer, physiological saline, or such, and then lysed using, singly or in combination, physical means such as freeze-thawing, sonication, pressure treatment, treatment with osmolality difference, and grinding, or a biochemical treatment, such as treatment with a cell wall-lysing enzyme, e.g., lysozyme, or chemical treatment, such as treatment with a detergent. Thus, D-aminoacylase can be extracted. A crude D-aminoacylase thus obtained can be purified by using, singly or in combination, means including salting out, fractional precipitation using organic solvents or such; separation methods of various chromatographic procedures including salting-out chromatography, ion-exchange chromatography, gel filtration chromatography, hydrophobic chromatography, dye chromatography, hydroxyapatite chromatography, affinity chromatography, or such, using an open column, medium-pressure chromatography or high-performance liquid chromatography (HPLC); electrophoretic separation methods, such as isoelectric focusing, native gel electrophoresis, and others.

Specifically, for example, microbial cells collected by filtration or centrifugation are frozen or disrupted, and then suspended in a buffer. The cells are disrupted using Bead-Beater (BIOSPEC PRODUCT) to prepare extract of the wild-type or mutant D-aminoacylase. Then, the extract is treated by salting-out using ammonium sulfate. The enzyme can be purified to homogeneity (single band in SDS-polyacrylamide gel electrophoresis) by hydrophobic chromatography using Phenyl-Sepharose FF and Mono Q ion-exchange chromatography.

The rate constants of the reaction with N-acetyl-D-tryptophan and N-acetyl-L-tryptophan that is catalyzed by the thus-purified wild-type derived from *Alcaligenes denitrificans* subsp. *xylosoxydans* MI-4 or mutant D-aminoacylases of the present invention, can be determined according to the methods described in "Lectures for Biochemical Experiments 21: Introduction to Experimental Approach to Enzyme Kinetics" and "Basic Experimental Methods for Proteins and Enzymes, 2nd Ed." Michaelis constant is represented by $K_m$; the maximal rate is $V_{max}$; inhibition constant is $K_i$; the constant for reaction inhibition by excess substrate is $K_s'$.

The present invention also relates to a method for producing D-tryptophan using a D-aminoacylase of the present invention, a transformant expressing the D-aminoacylase, or a processed product thereof.

D-aminoacylases of the present invention can produce D-amino acids from various N-acyl-D-amino acids. D-aminoacylases of the present invention are useful in producing D-amino acids on an industrial scale. For example, D-aminoacylases of the present invention can be allowed to act on N-acyl-DL-amino acid that is a mixture of D and L forms to specifically produce D-amino acid. More specifically, the present invention relates to a method for producing D-amino acid, which comprises the steps of contacting N-acyl-DL-amino acid with at least one enzymatically active substance selected from the group consisting of (a) to (c) and recovering the D-amino acid produced:

(a) a D-aminoacylase protein of the present invention;

(b) transformants expressing a D-aminoacylase of the present invention; and (c) processed products of transformants expressing a D-aminoacylase of the present invention.

There is no limitation on the type of N-acyl-DL-amino acid that can be used in the present invention, and such an amino acid can be selected from a wide range of compounds. A representative N-acyl-DL-amino acid is shown in formula (1).

Formula 1:

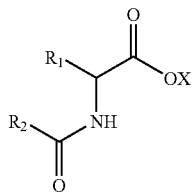

(I)

in which $R_1$ and $R_2$ are identical or different and selected from an alkyl group, an alkenyl group, an alkynyl group, a cycloalkyl group, an allyl group, and an aralkyl group. These groups may be substituted with a halogen atom, a single-chain alkoxyl group, a nitro group, a hydroxyl group, or such. More specifically, preferred substituents of $R_2$ include a methyl group, a chloromethyl group, and a phenyl group. Preferred $R_1$ include the substituents listed below. The name of N-acyl-DL-amino acid containing each substituent is indicated in parenthesis.

An indolyl group (N-acyl-DL-tryptophan)
A benzyl group (N-acyl-DL-phenylalanine)
A thiomethylethyl group (N-acyl-DL-methionine)
An isopropyl group (N-acyl-DL-valine)
A 2-methyl-propyl group (N-acyl-DL-leucine)

Preferred N-acyl-DL-amino acids used in the present invention include N-acetyl-DL-amino acids. Specific examples of N-acetyl-DL-amino acids are shown below. Among the N-acetyl-DL-amino acids, N-acetyl-DL-tryptophan is especially useful as a substrate in producing D-tryptophan that is an industrially important compound.

N-acetyl-DL-methionine
N-acetyl-DL-valine
N-acetyl-DL-tryptophan
N-acetyl-DL-asparagine
N-acetyl-DL-phenylalanine
N-acetyl-DL-alanine
N-acetyl-DL-leucine Any of the materials (a) to (c) having the enzyme activity described above can be used in production methods of the present invention. The materials having the enzyme activity to be used include the partially purified enzyme, transformants capable of producing the D-aminoacylase and processed products thereof in addition to the purified enzyme. Specifically, D-amino acid can be produced by directly contacting N-acetyl-DL-amino acid with a transformant capable of producing the D-aminoacylase or a processed product thereof.

As used herein, the phrase "processed product of a transformant" refers to a product yielded from a transformant by a physical treatment, such as freeze-thawing, sonication, pressure treatment, treatment with osmolality difference, or grinding; or a biochemical treatment, such as treatment with a cell wall-lysing enzyme, e.g., lysozyme, or chemical treatment, such as treatment with a detergent, or an organic solvent, such as toluene, xylene or acetone. Microorganisms whose cell membrane permeability has been altered by such a treatment, cell-free extract obtained from cells of microorganisms by lysing the cells with glass beads or an enzyme, and materials partially purified from them are all included in the processed products.

In general, enzymes and microorganisms are stabilized by immobilization. The immobilization can be achieved by a known method, such as polyacrylamide gel method, sulfated polysaccharide gel method (carrageenan gel method), alginate gel method, and agar gel method, which comprises conjugating with ion-exchange resins. Time required for the reaction with an immobilized enzyme or microorganism depends on the amounts of both D-aminoacylase and substrate. Those skilled in the art can select empirically an optimal condition considering these parameters. Typically, a reaction product of interest can be obtained with high efficiency by incubating for 10 to 100 hours.

The condition, where a D-aminoacylase of the present invention, transformant capable of producing the D-aminoacylase, or a processed product thereof is incubated with N-acyl-D-amino acid, is selected so as to be preferable to the activity and stability of the D-aminoacylase and the reactivity of a strain of transformant capable of producing the D-aminoacylase. The activity of D-aminoacylases of the present invention is sometimes enhanced or inhibited by a divalent metal ion, such as $Zn^{2+}$, $Ni^{2+}$, and $Co^{2+}$. If the enzymes are inhibited by a divalent metal ion, a chelating agent, such as EDTA, may be added to the reaction solution.

There is no limitation on the concentration of N-acyl-DL-amino acid that is the reaction substrate. Typically, the substrate is used at a concentration of about 0.1 to 50%, preferably 1 to 40%, more preferably 5 to 30%. In the reaction using an enzyme or cell of the present invention, N-acyl-DL-amino acid that is used as the substrate is a mixture of N-acyl-D-amino acid and N-acyl-L-amino acid. There is no limitation on the ratio of D form and L form in the mixture (D form:L form). Typically, the ratio ranges from 10:90 to 90:10, preferably from 25:75 to 75:25, more preferably is 50:50. When the ratio is 50:50, the mixture is referred to as racemate of N-acyl-amino acid.

As used herein, the phrase "high concentration of N-acetyl-DL-tryptophan" means 120 g/l or higher concentration of N-acetyl-DL-tryptophan, preferably 150 g/l or higher concentration of N-acetyl-DL-tryptophan, more preferably 200 g/l or higher concentration of N-acetyl-DL-tryptophan.

As used herein, the unit "%" means "weight/volume (w/v)". The "reaction yield" reaches 100% when all N-acetyl-D-tryptophan molecules contained in the reaction solution are converted to D-tryptophan.

The substrate may be added at once at the time of starting reaction or added continuously or stepwise to the reaction solution. The D-aminoacylases are used typically at a concentration of about 0.01 to 100000 U/ml, preferably about 0.1 to 10000 U/ml, more preferably about 1 to 1000 U/ml. There is no limitation on the reaction temperature, as long as the enzymes of the present invention are active and thus the reaction proceeds at the temperature. The reaction temperature ranges typically from 5 to 70° C., preferably from 10 to 50° C., more preferably from 20 to 40° C. There is also no limitation on the pH in the reaction, as long as the enzyme of the present invention is active and thus the reaction proceeds at the pH. The pH in the reaction ranges typically from 3 to 11, preferably from 5 to 10, more preferably from 6 to 9. The reaction can be carried out while the solution is being stirred or allowed stand still.

For example, D-tryptophan can be produced in 80% or higher yield by combining equal volumes of 40% N-acetyl-DL-tryptophan and the culture medium of transformants expressing a mutant D-aminoacylase that contains the mutations A154V/M347A/R374F and then incubating the mixture at 30° C. for 24 hours while being stirred.

D-amino acid produced in the reaction solution can be recovered by a known method, for example, concentration, direct crystallization by isoelectric point precipitation or such, the treatment with ion-exchange resins, filtration, etc. For example, when D-tryptophan is produced from N-acetyl-DL-tryptophan as a substrate, D-tryptophan is isolated from the reaction solution by flowing the reaction solution through strongly acidic cation-exchange resins for adsorption of D-tryptophan, washing the resins with water, and then eluting with 0.5 N ammonia water. The crystalline powder of crude D-tryptophan obtained by concentrating the eluate is dissolved in a small volume of hot 1:1 ethanol-water and then decolorized using activated carbon. Crystals of D-tryptophan is given by cooling the mixture.

With the D-amino acid-producing methods of the present invention, N-acyl-L-amino acid is not consumed in the reaction. The N-acyl-L-amino acid remained can be recycled by converting it to N-acyl-DL-amino acid with racemization. Methods for racemizing N-acyl-L-amino acids using enzymatic reaction (JP-A No. Hei 1-137973) or chemical reaction (Biochem. Z., 203, 280 (1929)) have been established.

The present invention enables highly efficient production of mutant D-aminoacylases whose substrate inhibition by N-acetyl-D-tryptophan or/and competitive inhibition by N-acetyl-L-tryptophan are reduced.

Mutant D-aminoacylases of the present invention can be used to stereoselectively hydrolyze higher concentrations of N-acetyl-DL-tryptophan to thereby produce D-tryptophan with improved productivity. The substrate inhibition and competitive inhibition of D-aminoacylases of the present invention are impaired so that the enzymes hydrolyzes N-acetyl-D-tryptophan as a substrate from N-acetyl-DL-tryptophan at a high concentration such as 200 g/l to produce D-tryptophan in 80% or higher yield. To date, no such D-aminoacylases have been available. D-tryptophan, which can be synthesized in high yield using D-aminoacylases of the present invention, is useful as a starting material to produce medicaments and others.

EXAMPLES

The present invention is illustrated in detail below with reference to Examples, but is not to be construed as being limited thereto.

Example 1

Preparation of Chromosomal DNA from *Alcaligenes denitrificans* subsp. *xylosoxydans* MI-4 Strain Chromosomal DNA was purified from the *Alcaligenes denitrificans* subsp. *xylosoxydans* MI-4 strain (FERM P-9413) according to the method described in Nucleic Acids Res. 8, 4321 (1980).

Example 2

Cloning of the D-aminoacylase Gene from *Alcaligenes denitrificans* subsp. *xylosoxydans* MI-4 Strain by PCR The sense primer ADD-ATG1 (SEQ ID NO: 1) and the antisense primer ADD-TGA1 (SEQ ID NO: 5) corresponding to the 5'- and 3'-untranslated regions of the D-aminoacylase gene from *Alcaligenes xylosoxydans* subsp. *xylosoxydans* A-6 strain were synthesized according to a description in the reference (Biosci. Biotech. Biochem., 59, 2115(1995)). PCR reaction was carried out using a 50-µl reaction solution containing 70 ng of chromosomal DNA from *Alcaligenes denitrificans* subsp. *xylosoxydans* MI-4 strain, 1.0 U ExTaq DNA polymerase, Taq polymerase buffer, 0.2 mM dNTP, 5% DMSO, and the primers ADD-ATG1 and ADD-TGA1 (10 pmol each) by 30 cycles of denaturation at 94° C. for 30 seconds and extension at 72° C. for 2 minutes. The PCR yielded a high-specific PCR product of about 1.5 kbp.

Example 3

Sequencing of PCR Products

The DNA fragment obtained in Example 2 was purified by GFX Kit (Pharmacia). The DNA fragment purified was analyzed for the nucleotide sequence. Nucleotide sequence analysis of the DNA was carried out by PCR using BigDye Terminator Cycle Sequencing ready Reaction Kit (Applied Bio Systems) in a PRISM 310 Genetic Analyzer (Applied Bio Systems). The primers used are ADD-189R (SEQ ID NO: 6), ADD-524R (SEQ ID NO: 7), ADD-466F (SEQ ID NO: 8), ADD-1032R (SEQ ID NO: 9), ADD-987F (SEQ ID NO: 10), and ADD-TGA1.

The sequence obtained is shown in SEQ ID NO: 1. The nucleotide sequence of D-aminoacylase was compared with a known clone of D-aminoacylase from *Alcaligenes xylosoxydans* subsp. *xylosoxydans* A-6. When the first letter A of the initiation codon ATG is taken as 1, only two nucleotide substitutions, 360-T->C and 435-C->T, are found between the two clones. The amino acid sequences are completely identical to each other. In addition, the D-aminoacylase was compared with those of *Alcaligenes* sp. CMC3352 and CMC3353. The 11 nucleotide alterations, 4-T->G(Ser$^2$->Ala), 7-C->G(Gln$^3$->Glu), 41-C->T(Ala$^{14}$->Val), 234-T->C(Arg$^{78}$->Arg), 306-G->A(Ala$^{102}$->Ala), 363-T->G(Ser$^{121}$->Ser), 369-T->C(Arg$^{123}$->Arg), 450-A->G(Ser$^{150}$->Ser), 676-G->C(Gly$^2$->Arg), 718-G->C (Gly$^{240}$->Arg), and 724-G->A(Glu$^{242}$->Lys), were revealed, and of the 11 substitution, six give amino acid alterations.

Example 4

Cloning of the D-aminoacylase Gene from *Alcaligenes denitrificans* subsp. *xylosoxydans* MI-4 Strain by PCR-2

The sense primer ADD-ATG2 (SEQ ID NO: 11) and the antisense primer ADD-TAA2 (SEQ ID NO: 12) were synthesize based on the nucleotide sequence of the DNA fragment determined in Example 3. PCR reaction was carried out using a 50-μl reaction solution containing 10 ng of PCR products obtained in Example 2 as a template, 2.5 U PfuTurbo DNA polymerase, PfuTurbo buffer, 0.2 mM dNTP, 5% DMSO, and the primers ADD-ATG2 and ADD-TGA2 (10 pmol each) by 30 cycles of denaturation at 95° C. for 30 seconds and extension at 72° C. for 160 seconds. The PCR yielded a high-specific PCR product of about 1.5 kbp.

Example 5

Construction of Expression Plasmids Containing the D-aminoacylase Gene

The DNA fragment obtained in Example 4 was purified with GFX Kit (Pharmacia), and then double-digested with the restriction enzymes EcoRI and HindIII. The DNA was electrophoresed in an agarose gel. A band of interest was excised from the gel and then purified with Sephaglas (Pharmacia).

Using T4 DNA ligase, the resulting DNA fragment was ligated with pSE420D (JP-A No. 2000-189170) that had been double-digested with the same restriction enzymes. Cells of *E. coli* JM109 strain were transformed with the ligated DNA.

The transformants were grown on LB plates containing ampicillin (50 μg/ml). Plasmids were purified from some colonies, and the nucleotide sequences of the insert fragments were determined. Each of Plasmids containing the D-aminoacylase gene was denominated as pSL-ADD2, pSL-ADD3, pSL-ADD4, and pSL-ADD5, respectively. The nucleotide sequences of the D-aminoacylase gene in the plasmids were compared with these nucleotide sequence of the PCR products obtained in Example 2 (the nucleotide sequence of D-aminoacylase from the original *Alcaligenes denitrificans* subsp. *xylosoxydans* MI-4). When the first letter A of the initiation codon ATG of the ORF is taken as 1, 679-GAG had been substituted to GGG (Glu$^{227}$->Gly) and 991-AAG had been substituted to AGG (Lys$^{331}$->Arg) in pSL-ADD2; and 1012-CTG had been substituted to CCG (Leu$^{338}$->Pro) in pSL-ADD4. D-aminoacylase activity was hardly detectable with pSL-ADD2 or pSL-ADD4. These amino acid substitutions were found to result in loss of the catalytic activity of the D-aminoacylase.

In pSL-ADD3, 103-GGC had been substituted to GAC (Gly$^{35}$->Asp), 634-AGC had been substituted to AGT (Ser$^{212}$->Ser), and 973-GCC had been substituted to GCT (Ala$^{325}$->Ala); and in pSL-ADD5, 43-GGC had been substituted to GGA (Gly$^{15}$->Gly), and 1009-GAG had been substituted to GGG (Glu$^{337}$->Gly). Nonetheless, the enzymes encoded by pSL-ADD3 and pSL-ADD5 were confirmed to have the D-aminoacylase activity, and thus the amino acid substitutions were found to exert no influence on the catalytic activity of the D-aminoacylase.

Example 6

Preparation of Modified D-aminoacylase Genes that are Compatible to the Codon Usage in *E. coli*

(1) Construction of expression plasmids containing the modified D-aminoacylase genes The D-aminoacylase gene derived from *Alcaligenes denitrificans* subsp. *xylosoxydans* MI-4 strain contains, in its coding region, some codons corresponding to rare codons in *E. coli*, and its GC content is exceedingly high. To improve both stability and expression efficiency of the D-aminoacylase gene in *E. coli*, the nucleotide substitutions generated during the PCR cloning described in Example 4 were corrected and the codons corresponding to rare codons in *E. coli* were removed from the D-aminoacylase gene. In addition, codons were changed to be compatible to the codon usage of the host *E. coli*, and the GC content in the coding region was also adjusted to be compatible to *E. coli*. The nucleotide sequence was re-constructed by designing it not to alter the amino acid sequence due to the nucleotide sequence modifications. The nucleotide sequence of the resulting DNA is shown in SEQ ID NO: 3.

The dsDNA was synthesized based on the information on the nucleotide sequence of the modified D-aminoacylase gene which was designed to contain PciI and XbaI recognition sites at the two end, respectively. The dsDNA was integrated into a pUC vector by the oligo DNA assembling method. After the nucleotide sequence of the clone obtained was verified, the DNA was double-digested with PciI and XbaI. Using T4 DNA ligase, the DNA was ligated with pSE420D which had been double-digested with NcoI and XbaI to prepare the plasmid pSL-ADD6 that enables the expression of the modified D-aminoacylase gene. The plasmid pSL-ADD6 containing the modified D-aminoacylase gene was deposited under the accession number FERM BP-08508 in International Patent Organism Depositary, National Institute of Advanced Industrial Science and Technology (AIST), Independent Administrative Institution on Nov. 12, 2002. Cells of *E. coli* JM109 strain were transformed with the plasmid.

(2) Assay for the activity of D-aminoacylase produced from the modified D-aminoacylase gene The transformant obtained in Example 5 (1) was cultured in a liquid LB medium containing ampicillin (50 μg/ml) at 26° C. overnight while being shaken. After 0.1 mM IPTG was added to the culture. The cells were incubated at 30° C. for another four hours while being shaken. The bacterial cells were collected by centrifugation, and then suspended in 100 mM Tris-hydrochloride buffer (pH 9.0) containing 0.02% 2-mercaptoethanol. The cells were lysed by sonication in a tight-sealed sonicator UCD-20OTM (Cosmo Bio) for three minutes. The bacterial cell lysate was centrifuged, and the resulting supernatant was recovered as cell extract. The extract was assayed for the D-aminoacylase activity. While the activity of wild-type D-aminoacylase was found to be 34 U/mg, the activity of D-aminoacylase produced with the modified D-aminoacylase gene was 86 U/mg. The nucleotide sequence modifications were confirmed to contribute to the improvement of the specific activity.

Example 7

PCR Mutagenesis for the D-aminoacylase Derived from *Alcaligenes denitrificans* subsp. *xylosoxydans* MI-4

Random nucleotide substitutions were introduced into the nucleotide sequence of the D-aminoacylase gene by replicating the D-aminoacylase gene by the PCR method with a low-fidelity DNA polymerase using the expression vector pSL-ADD6 for the D-aminoacylase which had been constructed in Example 6. Transformants were obtained by transforming cells of *E. coli* JM109.

The primers ADD-ATG2 and ADD-TAA2 were used to amplify the DNA fragment of interest. PCR reaction was conducted in a 50-µl reaction solution containing Taq polymerase buffer, 0.2 mM DNTP, and the primers ADD-ATG2 and ADD-TAA2 (10 pmol each), 2.0 U Taq DNA polymerase, and 125 ng of pSL-ADD6 by 30 cycles of denaturation at 94° C. for 30 seconds and extension at 72° C. for 105 seconds. The resulting PCR fragment was double-digested with EcoRI and HindIII. Using T4 DNA ligase, the PCR fragment treated with the restriction enzymes was ligated with pSE42OD that had been double-digested with EcoRI and HindIII to prepare a library of plasmids containing the D-aminoacylase genes having various random nucleotide substitutions. A library of transformants containing the D-aminoacylase genes having mutations was prepared by transforming cells of *E. coli* JM109 strain with the plasmid library.

Example 8

Screening for Mutants

Cells of the *E. coli* transformant were inoculated on an LB agar plate. Each colony grown on the plate was inoculated with a toothpick to a well of a microtiter plate which contained 150 µl of LB culture medium containing 50 µg/ml ampicillin and 0.02 mM IPTG, and then the microtiter plate was covered with Breathable Sealing Membrane (Nalgene). The microtiter plate was incubated at 37° C. for 18 hours while being shaken. 10 µl of the culture medium solution was added to the reaction solution containing 300 mM Tris-hydrochloride buffer (pH 8.0), 0.1% cetylpyridinium bromide, 5% N-acetyl-DL-tryptophan, 1% N-acetyl-L-tryptophan, and distilled water in the wells of a microtiter plate. The plate was incubated at 25° C. for 1 hour while being shaken. Then, D-tryptophan produced from N-acetyl-D-tryptophan was quantified by colorimetry according to the TNBS method.

The wild-type strain was also used simultaneously in the reaction. After reaction, strains were selected whose activity of producing D-tryptophan was higher than that of the wild type. A screening of about 3000 colonies yielded four mutant strains. The four mutant strains obtained were cultured in LB culture media containing 50 µg/ml ampicillin and 0.02 mM IPTG at 30° C. for 18 hours while being shaken. The liquid culture media were incubated in the presence of 5% N-acetyl-DL-tryptophan and 1% N-acetyl-L-tryptophan. By comparing the amount of D-tryptophan released with that of the wild type, the degree of inhibition of D-tryptophan production by N-acetyl-L-tryptophan was confirmed to be reduced. Thus, the four mutant D-aminoacylases, AD-0103, AD-1064, AD-1089, and AD-1927, were obtained by the procedure described above.

Example 9

Analysis for Mutation Sites in Mutant D-aminoacylases

The recombinant DNAs containing the mutant genes were purified from *E. coli* transformants by a conventional method. The thus-obtained nucleotide sequences of mutant enzyme genes, whose inhibition is impaired, were analyzed. According to the result, in both of the mutant D-aminoacylases AD-0103 and AD-1089, Val residues (GTG) had been substituted for Met residues at position 347 (ATG). In the mutant D-aminoacylase AD-1064, Val residue (GTC) had been substituted for Ala residue (GCC) at position 154. In the mutant D-aminoacylase AD-1927, Thr residue (ACC) had been substituted for Ala residue (GCC) at position 154; and His residue (CAC) had been substituted for Arg residue at position 374 (CGC). These amino acid substitutions were not found in any of the sequences previously disclosed for D-aminoacylases belonging to the genus *Alcaligenes*.

Example 10

Effect of Mutants on Conversion of Higher Concentrations of N-acetyl-DL-tryptophan Cells of *E. coli* HB101 strain were transformed with the expression plasmids for the three mutant D-aminoacylases AD-0103, AD-1064, and AD-1927 obtained in Example 8, whose inhibition was impaired. The *E. coli* cells were inoculated in liquid LB media, and cultured at 30° C. overnight. Then, the transformants were inoculated in 2x YT (2% Bacto tryptone, 1% Bacto-yeast extract, 1.0% sodium chloride, pH 7.2) media and incubated at 30° C. for 18 hours. The *E. coli* cells were harvested. The bacterial cells were used to hydrolyze N-acetyl-D-tryptophan.

Cells of the respective *E. coli* transformants prepared from 5 ml of liquid culture media were incubated in 10 ml of reaction solutions which comprised 300 mM Tris-hydrochloride buffer (pH 8.0) containing 5% or 10% N-acetyl-DL-tryptophan at 25° C. while being stirred. An *E. coli* HB101 strain containing the plasmid pSL-ADD6 with the wild-type D-aminoacylase was used as a control. In assays using 5% N-acetyl-DL-tryptophan as the substrate, the yield was about 50% with the wild type, whereas the yield was about 100% with any one of the four mutants. In assays using 10% N-acetyl-DL-tryptophan as the substrate, the yield was about 15% with the wild type, whereas the yield was about 25% with each of the mutants AD-0103 and AD-1089; the yield was about 40% with the mutant AD-1064, and the yield was about 60% with the mutant AD-1927. The mutants obtained in Example 8, whose inhibition is impaired, were confirmed to have higher processibility in the conversion from higher concentrations of N-acetyl-DL-tryptophan.

Example 11

Preparation of the Second Generation Mutants

Random mutations were introduced into the gene at the positions corresponding to Ala at position 154, Met at position 347, and Arg at position 374, at which mutations were found to contribute to the impairment of the substrate inhibition and/or competitive inhibition in Example 9. Then, a screening was carried out to identify more effective amino acid residues.

The primers indicated below were synthesized: the primers ADDm-55F (SEQ ID NO: 13) and ADDm-460mix (SEQ ID NO: 14) to be used for randomly substituting another amino acid residue for Ala at position 154; the primers ADDm-627F (SEQ ID NO: 15) and ADDm-1039mix (SEQ ID NO: 16) to be used for randomly substituting another amino acid residue for Met at position 347; and the primers ADDm-627F and ADDm-1120mix (SEQ ID NO: 17) to be used for randomly substituting another amino acid residue for Arg at position 374 of the D-aminoacylase from *Alcaligenes denitrificans* subsp. *xylosoxydans* MI-4. With the expression vector pSL-ADD6 containing the modified D-aminoacylase gene constructed in Example 6, mutations were introduced at positions of interest through random amino acid substitution by PCR using these primers.

PCR was carried out using each primer set and the plasmid pSL-ADD6 as the template (25 cycles of denaturation at 95° C. for 30 seconds, annealing at 60° C. for 60 seconds, and extension at 72° C. for 60 seconds) The PCR-amplified fragment obtained using the pair of ADDm-55F and ADDm-460mix was double-digested with AvaI and BglII; the PCR-amplified fragment obtained using the pair of ADDm-627F and ADDm-1039mix was double-digested with BlpI and BsrGI; and the PCR-amplified fragment obtained using the pair of ADDm-627F and ADDm-1120mix was double-digested with BlpI and KpnI. With T4 DNA ligase, each of the PCR-amplified fragments digested with the restriction enzymes was ligated with pSL-ADD6 which had been double-digested with the same restriction enzymes. Thus, the following mixtures were obtained: a mixture of plasmids in which another amino acid residue had been substituted for Ala at position 154 at random; a mixture of plasmids in which another amino acid residue had been substituted for Met at position 347 at random; and a mixture of plasmids in which another amino acid residue had been substituted for Arg at position 374 at random. Cells of *E. coli* JM109 strain were transformed separately with each of the three plasmid libraries to construct three types of libraries.

Example 12

Screening for the Second Generation Mutants

Three types of the *E. coli* transformant libraries obtained in Example 11 were inoculated on an LB agar plate. Each colony grown on the plate was inoculated with a toothpick to a well of a microtiter plate which contained 150 µl of LB culture medium containing 50 µg/ml ampicillin and 0.02 mM IPTG, and then the microtiter plate was covered with Breathable Sealing Membrane (Nalgene). The microtiter plate was incubated at 37° C. for 18 hours while being shaken. 10 µl of the culture medium solution was added to the reaction solution containing 300 mM Tris-hydrochloride buffer (pH 8.0), 0.1% cetylpyridinium bromide, 5% N-acetyl-DL-tryptophan, 1% N-acetyl-L-tryptophan, and distilled water in the wells of a microtiter plate. The plate was incubated at 25° C. for 1 hour while being shaken. Then, D-tryptophan produced from N-acetyl-D-tryptophan was quantified by colorimetry according to the TNBS method. The same reaction as described above was conducted simultaneously using wild-type *E.coli* strain. Then, mutants with increased activity for producing D-tryptophan compared with wild-type strain were isolated as mutants with reduced inhibition. Screening of about 200 colonies yielded a number of mutants whose competitive inhibition had been reduced.

Example 13

Analysis of the Second Generation D-aminoacylase Mutants for Mutated Sites

The nucleotide sequences of the three types of the second generation mutant enzyme genes obtained in Example 12, whose inhibition was impaired, were determined. Strains, whose inhibition was found to be impaired, from each group of the *E. coli* transformants, were analyzed. The top 7, 18, and 18 strains were selected for A154X, M347X, and R374X, respectively, to analyze which amino acids had been substituted at each position. Recombinant DNAs containing the respective mutant genes were purified by a conventional method. The nucleotide sequences of the mutant D-aminoacylase genes in the recombinant DNAs were determined.

The amino acid substitution in each mutant, and the effect of the amino acid substitution, which was estimated as an activity of producing D-tryptophan in the presence of 5% N-acetyl-DL-tryptophan and 2% N-acetyl-L-tryptophan, are shown in Table 2. The "activity", as used herein, refers to "a colorimetric value of the reaction solution determined at the end of reaction by the TNBS method (Abs. 420)/the degree of bacterial growth (OD600)".

TABLE 2

| D-aminoacylase | 460-GCG 154-Ala | 1039-ATG 347-Met | 1120-CGC 374-Arg | Activity of producing D-tryptophan |
|---|---|---|---|---|
| wild-type | — | — | — | 2.58 |
| A154-0043 | GTA Val | — | — | 3.34 |
| A154-0170 | TGC Cys | — | — | 3.03 |
| A154-0183 | ACA Thr | — | — | 3.28 |
| M347-0025 | — | GGT Gly | — | 7.99 |
| M347-0033 | — | AAC Asn | — | 4.86 |
| M347-0073 | — | CAA Gln | — | 9.69 |
| M347-0078 | — | ATA Ile | — | 5.26 |
| M347-0086 | — | TCT Ser | — | 6.86 |
| M347-0130 | — | CCC Pro | — | 5.94 |
| M347-0146 | — | GCA Ala | — | 9.00 |
| R374-0017 | — | — | TTT Phe | 8.54 |
| R374-0030 | — | — | AAA Lys | 3.47 |
| R374-0036 | — | — | CTT Leu | 3.70 |
| R374-0062 | — | — | CAC His | 6.88 |
| R374-0092 | — | — | ATC Ile | 3.22 |
| R374-0132 | — | — | TGG Trp | 4.40 |
| R374-0177 | — | — | TAT Tyr | 5.86 |

Example 14

Preparation of Third Generation Mutants

Two types of mutant D-aminoacylases containing amino acid substitutions and showing especially impaired inhibition were selected from each group of the second generation mutants obtained in Example 13. Namely, the pairs were: A154-0043 (containing the amino acid substitution of A154V) and A154-0183 (containing the amino acid substitution of A154T); M347-0073 (containing the amino acid substitution of M347Q) and M347-0133 (containing the amino acid substitution of M347A); and R374-0017 (containing the amino acid substitution of R374F) and R374-0062 (containing the amino acid substitution of R374H). The third generation mutant enzymes, whose inhibition was further impaired, were identified by combining mutations at the respective sites. Hereinafter, the plasmid containing DNA encoding A154-0043 is referred to as "pA154-0043"; the plasmid containing DNA encoding A154-0183 is referred to as "pA154-0183"; the plasmid containing DNA encoding M347-0073 is referred to as "pM347-0073"; the plasmid containing DNA encoding M347-0133 is referred to as "pM347-0133"; the plasmid containing DNA encoding R374-0017 is referred to as "pR374-0017"; and the plasmid containing DNA encoding R374-0062 is referred to as "pR374-0062".

Both pA154-0043 and pA154-0183 were double-digested with the two restriction enzymes AvaI and BlpI. After ethanol precipitation, the DNAs were electrophoresed in an agarose gel. The bands of about 0.6 kbp were excised from the gel, and the DNAs were purified and recovered using Sephaglas BandPrep (Amersham Pharmacia Biotech). The DNA fragments of about 0.6 kbp derived from pA154-0043 and pA154-0183 contain the mutations A154V and A154T, respectively, and thus referred to as pA154-0043/AvaI/BlpI and pA154-0183/AvaI/BlpI, respectively. Both pM347-0073 and pM347-0133 were double-digested with the two restriction enzymes BlpI and BsrGI. After ethanol precipitation, the DNAs were electrophoresed in an agarose gel. The bands of about 0.4 kbp were excised from the gel, and the DNAs were purified and recovered using Sephaglas BandPrep (Amersham Pharmacia Biotech).

The DNA fragments of about 0.4 kbp derived from pM347-0073 and pM347-0133 contain the mutations M347Q and M347A, respectively, and thus referred to as pM347-0073/BlpI/BsrGI and pM347-0133/ BlpI/BsrGI, respectively. Both pR374-0017 and pR374-0062 were digested with the three restriction enzymes AvaI, BlpI, and BsrGI. After ethanol precipitation, the DNAs were recovered. The DNA fragments derived from pR374-0017 and pR374-0062 were about 0.6 kbp, about 0.4 kbp, and about 5 kbp in size, respectively. The mixtures of the three fragments are referred to as "pR374-0017/AvaI/BlpI/BsrGI" and "pR374-0062/AvaI/BlpI/BsrGI", respectively. The fragments of about 5 kbp in the two mixtures have the mutations R374F and R374H, respectively. pSL-ADD6 was digested with the three restriction enzymes AvaI, BlpI, and BsrGI. After ethanol precipitation, the DNA was recovered. The DNA fragments derived from pSL-ADD6 include fragments of about 0.6 kbp, about 0.4 kbp, and about 5 kbp all of which contain no amino acid substitution. A mixture of the three fragments is referred to as "pSL-ADD6/AvaI/BlpI/BsrGI".

[pR374-0017/AvaI/BlpI/BsrGI, pR374-0062/AvaI/BlpI/BsrGI, pSL-ADD6/AvaI/BlpI/BsrGI], [pA154-0043/AvaI/BlpI, pA154-0183/AvaI/BlpI], and [pM347-0073/BlpI/BsrGI, pM347-0133/BlpI/BsrGI] were combined together at the molar ratio of 1:3:3. The mixture was ligated at random with T4 DNA ligase. Thus, a plasmid mixture comprising mutants that respectively contain two amino acid substitutions and three amino acid substitutions generated through random combination of three types of mutations at each position of the three was obtained by the procedure described above. Cells of E. coli JM109 strain were transformed with the plasmid mixture to obtain transformants.

Example 15

Screening for the Three Generation Mutants

Cells of the E. coli transformant obtained in Example 9 were inoculated on an LB agar plate. Each colony grown on the plate was inoculated with a toothpick to a well of a microtiter plate which contained 150 µl of LB culture medium containing 50 µg/ml ampicillin and 0.02 mM IPTG, and then the microtiter plate was covered with Breathable Sealing Membrane (Nalgene). The microtiter plate was incubated at 37° C. for 18 hours while being shaken. 10 µl of the culture medium solution was added to the reaction solution containing 300 mM Tris-hydrochloride buffer (pH 8.0), 0.1% cetylpyridinium bromide, 2% N-acetyl-DL-tryptophan, 3.5% N-acetyl-L-tryptophan, and distilled water in the wells of a microtiter plate. The plate was incubated at 25° C. for 30 minutes while being shaken. Then, D-tryptophan produced from N-acetyl-D-tryptophan was quantified by colorimetry according to the TNBS method using D-tryptophan as standard. The same reaction as described above was conducted simultaneously using wild-type E. coli strain. Then, mutants in which the activity for producing D-tryptophan was increased compared with wild-type strain were isolated as mutants with reduced inhibition. Screening of about 200 colonies yielded a number of mutants whose competitive inhibition had been reduced.

Example 16

Analysis of the Third Generation Mutant D-aminoacylases for Mutation Sites

The nucleotide sequences of the third generation mutant enzyme genes obtained in Example 15, whose inhibition is impaired, were determined. According to a conventional method, recombinant DNAs containing the mutant genes were purified from the top 20 strains selected from each group of E. coli transformants, whose inhibition is impaired. The nucleotide sequences of the mutant D-aminoacylase genes in the recombinant DNAs were determined.

The amino acid substitutions in each mutant are shown in Table 3.

TABLE 3

| D-aminoacylase | 460-GCG 154-Ala | 1039-ATG 347-Met | 1120-CGC 374-Arg | Activity of producing D-tryptophan |
|---|---|---|---|---|
| wild-type | — | — | — | 2.65 |
| 3AD-0004 | ACA Thr | GCA Ala | TTT Phe | 3.78 |
| 3AD-0013 | — | CAA Gln | CAC His | 5.72 |
| 3AD-0029 | — | GCA Ala | TTT Phe | 3.69 |
| 3AD-0041 | — | GCA Ala | CAC His | 7.32 |
| 3AD-0063 | GTA Val | GCA Ala | — | 3.06 |

TABLE 3-continued

| D-aminoacylase | 460-GCG 154-Ala | 1039-ATG 347-Met | 1120-CGC 374-Arg | Activity of producing D-tryptophan |
|---|---|---|---|---|
| 3AD-0089 | GTA Val | GCA Ala | TTT Phe | 8.14 |
| 3AD-0093 | ACA Thr | CAA Gln | TTT Phe | 7.03 |
| 3AD-0109 | ACA Thr | GCA Ala | CAC His | 5.87 |
| 3AD-0136 | GTA Val | CAA Gln | CAC His | 8.43 |
| 3AD-0149 | ACA Thr | CAA Gln | CAC His | 6.36 |

Example 17

Assessment of the Activities of the Third Generation D-aminoacylase Mutants in the Reaction With a conventional method, recombinant plasmid DNAs were purified from total 10 strains of E. coli JM109 transformant obtained in Example 16. Cells of E. coli HB101 strain were transformed with the recombinant plasmid DNAs to prepare transformants. Each colony grown on a culture plate was inoculated with a toothpick to a well of a microtiter plate which contained 150 μl of LB culture medium containing 50 μg/ml ampicillin and 0.02 mM IPTG, and then the microtiter plate was covered with Breathable Sealing Membrane (Nalgene). The microtiter plate was incubated at 37° C. for 18 hours while being shaken. The reaction was carried out using total 200 μl of a reaction solution containing 100 μl of culture medium solution, 300 mM Tris-hydrochloride buffer (pH 8.0), 7% N-acetyl-DL-tryptophan, and distilled water in each well of a microtiter plate at 25° C. for 8 hours while being shaken. When all of the N-acetyl-D-tryptophan contained in substrate is converted to D-tryptophan, the yield is taken as 100%. While the yield was about 70% with the wild type, the yield was roughly 100% with a third generation mutant obtained in Example 11. Thus, the competitive inhibition was confirmed to be impaired in the third generation mutants.

Example 18

Selection of the Most Preferable Mutant

3AD-0013(M347Q/R374H) and 3AD-0089(A154V/M347A/R374P) are mutants with two amino acid substitutions and with three amino acid substitutions of the third generation mutants obtained in Example 17, respectively. Cells of E. coli HB101 strain transformed with plasmids expressing the two types of mutants were each inoculated to a liquid LB medium, and cultured at 30° C. overnight. Then, the E. coli cells were inoculated to a culture medium (2x YT) and incubated at 30° C. for 18 hours. The cells of E. coli were harvested, and used to hydrolyze N-acetyl-D-tryptophan.

10 ml of a reaction solution containing E. coli cells prepared from 5 mL of culture medium solution, 300 mM Tris-hydrochloride buffer (pH 8.0), and 15% N-acetyl-DL-tryptophan was incubated at 25° C. for 24 hours while being stirred. E. coli HB101 strain containing the wild-type pSL-ADD6 was used as a control. While the yield was about 15% with the wild type, the yields were about 30% and about 80% with the mutant 3AD-0013 having two amino acid substitutions and the mutant 3AD-0089 having three amino acid substitutions, respectively. Thus, the third generation mutants obtained in Example 15 were confirmed to have higher processability in the hydrolysis of higher concentrations of N-acetyl-DL-tryptophan.

Example 19

Purification of the Wild-type D-aminoacylase

An E. coli transformant containing the plasmid pSL-ADD6 containing DNA encoding the wild-type D-aminoacylase was inoculated to a liquid LB culture medium and cultured at 30° C. overnight. Then, the E. coli cells were inoculated to a culture medium (2×YT) and incubated at 30° C. overnight culture. The bacterial cells were harvested by centrifugation, and the resulting wet bacterial cells were suspended in a mixed solution comprising 100 mM phosphate buffer (pH 8.0), 0.02% 2-mercaptoethanol, and 2 mM phenylmethanesulfonyl fluoride (PMSF). After the cells were lysed with a bead beater (Biospec), the cell debris was removed by centrifugation to prepare cell-free extract. Protamine sulfate was added to the cell-free extract. The extract was centrifuged to remove nucleic acids. Ammonium sulfate was added to the resulting supernatant until it became 30% saturated. The mixture was loaded onto a column containing Phenyl-Sepharose HP (2.6 cm×10 cm) equilibrated with a standard buffer (10 mM phosphate buffer (pH 8.0), 0.01% 2-mercaptoethanol, and 10% glycerol) containing 30% ammonium sulfate. The sample was detected in a fraction eluted from the column using a gradient of 30% to 0% ammonium sulfate. The D-aminoacylase activity was eluted with the gradient. The peak fraction eluted was recovered and concentrated by ultrafiltration.

After the concentrated enzyme solution was dialyzed against the standard buffer, the resulting solution was loaded onto a Mono-Q column (1.6 cm×10 cm) equilibrated with the same buffer. Elution was carried out with a gradient of 0 to 0.5 M sodium chloride. An active fraction eluted was recovered and concentrated by ultrafiltration. Thus, a concentrated enzyme solution was obtained.

The specific activity of the purified enzyme was 528 U/mg.

Example 20

Purification of the Mutant Enzyme D-aminoacylase A154-0043 (containing the Amino Acid Substitution of A154V)

The mutant D-aminoacylase A154-0043 was purified from an E. coli transformant having the plasmid pSL-AD07 that contains DNA encoding the mutant D-aminoacylase A154-0043 by the same method as described in Example 19.

The specific activity of purified enzyme was 758 U/mg.

Example 21

Purification of the Mutant Enzyme D-aminoacylase M347-0133 (containing the Amino Acid Substitution of M347A)

The mutant D-aminoacylase M347-0133 was purified from an E. coli transformant having the plasmid pSL-AD08 that contains DNA encoding the mutant D-aminoacylase M347-0133 by the same method as described in Example 19.

The specific activity of purified enzyme was 1099 U/mg.

Example 22

Purification of the Mutant Enzyme D-aminoacylase R374-0017 (containing the Amino Acid Substitution of R374F)

The mutant D-aminoacylase R374-0017 was purified from an *E. coli* transformant having the plasmid pSL-AD09 that contains DNA encoding the mutant D-aminoacylase R374-0017 by the same method as described in Example 19.

The specific activity of purified enzyme was 855 U/mg.

firmed to be impaired in the reaction using any of the mutant D-aminoacylases.

With 3AD-0089 (containing the amino acid substitution of A154V/M347A/R374F) in particular, the substrate inhibition was not detectable even in the presence of 99 mM N-acetyl-D-tryptophan, and the competitive inhibition was not detectable even in the presence of 89 mM N-acetyl-L-tryptophan. Thus, the mutations were confirmed to largely contribute to the impairment of the inhibition.

TABLE 4

|  | D-aminoacylase | | | | |
| --- | --- | --- | --- | --- | --- |
|  | wild-type | A154-0043 | M347-0133 | R374-0017 | 3AD-0089 |
|  | | Amino acid substitution | | | |
|  | — | A154V | M347A | R374F | A154V M347A R374F |
| $K_m$[b] Lineweaver-Burk reciprocal plot) | 2.53 | 3.44 | 1.42 | 1.94 | 1.46 |
| $V_{max}$[b] (Lineweaver-Burk reciprocal plot) | 685 | 1031 | 1000 | 1000 | 357 |
| $K_i$[c] (Second-order plot; Royer, 1982)) | 2.60 | 6.40 | 12.27 | 7.46 | N.D.[d] |
| $K_s$'[b] ([S]−1/v plot) | 1.29 | 13.67 | 77.00 | 93.00 | N.D.[d] |

[a] Measurements at 30° C., pH7.5
[b] Reaction rate constant for N-acetrl-D-typtophan
[c] Reaction rate constant for N-acetrl-L-typtophan
[d] N.D.: not detected

Example 23

Purification of the Mutant Enzyme D-aminoacylase 3AD-0089 (containing the Amino Acid Substitution of A154V/M347A/R374F)

The mutant D-aminoacylase 3AD-0089 was purified from an *E. coli* transformant having the plasmid pSL-AD10 that contains DNA encoding the mutant D-aminoacylase 3AD-0089 by the same method as described in Example 19.

The specific activity of purified enzyme was 324 U/mg in about 70% purity.

Example 24

Tests of the Mutant D-aminoacylase for the Inhibition by N-acetyl-D-tryptophan and N-acetyl-L-tryptophan The D-aminoacylases purified in Examples 20 to 23 were tested for the inhibition by N-acetyl-D-tryptophan and N-acetyl-L-tryptophan. The reaction rate constants for N-acetyl-D-tryptophan and N-acetyl-L-tryptophan were determined according to the methods described in "Lectures for Biochemical Experiments 21: Introduction to Experimental Approach to Enzyme Kinetics" and "Basic Experimental Methods for Proteins and Enzymes, 2nd Ed." Michaelis constant is represented by $K_m$; the maximal rate is $V_{max}$; inhibition constant is $K_i$; the constant for reaction inhibition by excess substrate is represented by $K_s'$. $K_m$ and $V_{max}$ were determined from a Lineweaver-Burk reciprocal plot; $K_i$ was determined from a second-order plot (Royer); and $K_s'$ was determined from a [S] −1/v plot. The results are shown in Table 4.

Both substrate inhibition by N-acetyl-D-tryptophan and competitive inhibition by N-acetyl-L-tryptophan were con-

Example 25

Production of D-tryptophan from N-acetyl-DL-tryptophan using the Wild Type and Mutant D-aminoacylase 0.5 ml of a reaction solution containing 5 units of cell-free extract obtained in the step of enzyme purification described in Example 19 or Example 23, 12%, 15%, 17%, 20%, or 22% N-acetyl-DL-tryptophan, and 300 mM Tris-hydrochloride buffer (pH 8.0) was incubated at 30° C. for 24 hours while being stirred. The result obtained is shown in Table 5. While with the wild type the yield of D-tryptophan was lower than 10% at any substrate concentration, with the mutant 3AD-0089 the yield of D-tryptophan was 80% or higher at substrate concentrations of up to 17%. Furthermore, the mutant was confirmed to enable the production of D-tryptophan in 66% yield in the presence of 20% substrate, or in 58% yield in the presence of 22% substrate.

TABLE 5

|  | Yield of D-Trp (%) | |
| --- | --- | --- |
| Substrate N-Ac-DL-Trp (%) | wild-type (10 U/mL- Reaction solution) | 3AD-0089 (10 U/mL- Reaction solution) |
| 12 | 9.4 | 98.5 |
| 15 | 3.5 | 98.5 |
| 17 | 1.8 | 87.4 |
| 20 | 0.5 | 65.9 |
| 22 | 0.5 | 58.1 | a) N-Ac-DL-Trp: N-acetyl-DL-tryptophan, D-Trp: D-tryptophan
b) wild-type: Wild type D-aminoacylase, 3AD-0089: Mutant D-aminoacylase

Example 26

Production of D-tryptophan from High Concentrations of N-acetyl-DL-tryptophan Using a Recombinant *E. coli* Having the Plasmid pSL-AD10 that Contains DNA Encoding the Mutant D-aminoacylase 3AD-0089 (Containing the Amino Acid Substitution of A154V/M347A/R374F)

Cells of *E. coli* HB101 strain were transformed with the plasmid pSL-AD10 expressing the mutant D-aminoacylase 3AD-0089 (containing the amino acid substitution of A154V/M347A/R374F) obtained in Example 18. The transformant was inoculated to a liquid LB medium, and cultured at 30° C. overnight. Then, the *E. coli* was inoculated to a culture medium (2x YT) and incubated at 30° C. for 18 hours. N-acetyl-D-tryptophan was hydrolyzed using the culture medium solution of the *E. coli*.

400 mL of a reaction solution containing the culture medium solution of the *E. coli* and 15% N-acetyl-DL-tryptophan was incubated at 30° C. for 24 hours while being stirred. *E. coli* HB101 strain containing the wild type pSL-ADD1 was used as a control. The result obtained is shown in FIG. 1. While with the wild type the yield was about 4%, with the recombinant *E. coli* containing pSL-AD10 the yield was 90% or higher (FIG. 1).

Example 27

Production of D-tryptophan from High Concentrations of N-acetyl-DL-tryptophan Using a Recombinant *E. coli* Having the Plasmid pSL-AD10 that Contains DNA Encoding the Mutant D-aminoacylase 3AD-0089 (Containing the Amino Acid Substitution of A154V/M347A/R374F)-2—

Figure 2:
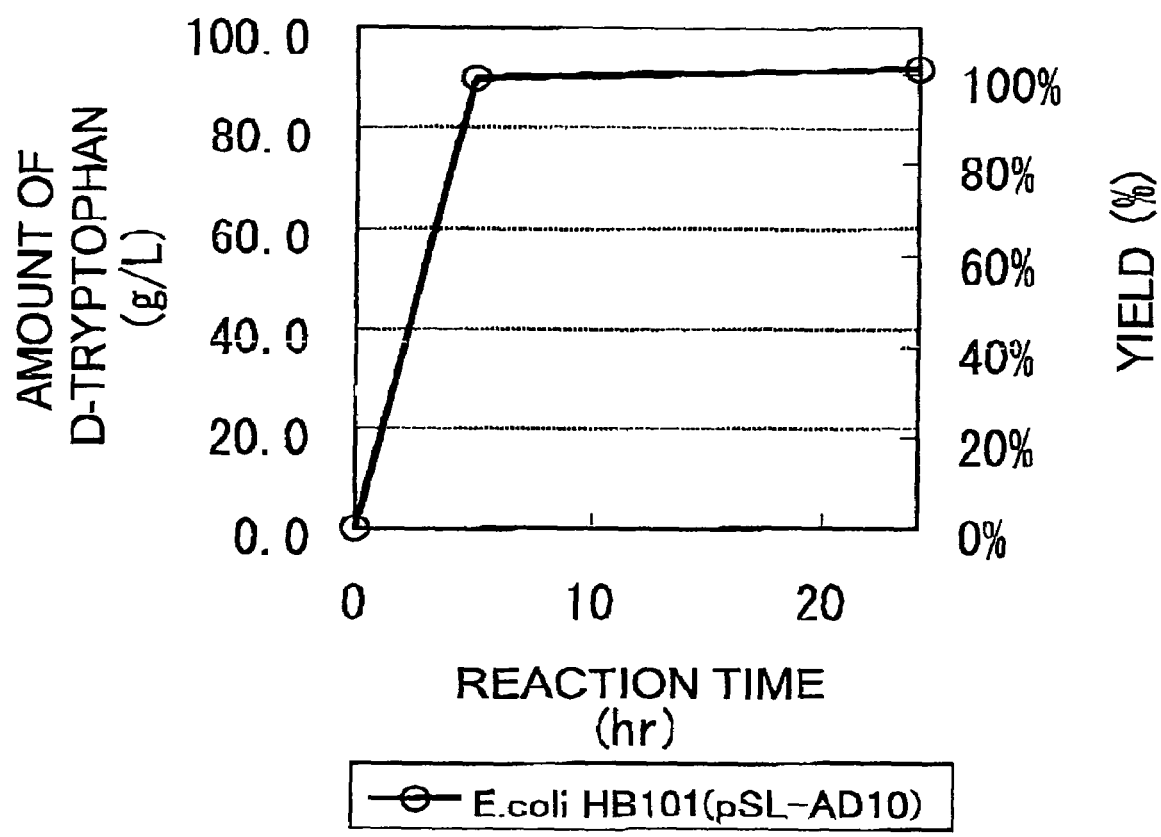
FIG. 2 shows production of D-tryptophan through the hydrolysis of 20% N-acetyl-DL-tryptophan using a culture medium of recombinant *E. coli* producing mutant D-aminoacylase. The ordinate axis indicates the amount of D-tryptophan produced (g/l) or yield (%); the abscissa axis indicates the reaction time (h).

The hydrolysis was carried out in the presence of 20% N-acetyl-DL-tryptophan by the same method as described in Example 26. The result obtained is shown in FIG. 2. The yield was 90% or higher with the recombinant *E. coli* having the plasmid pSL-AD10 that contains the DNA encoding the mutant D-aminoacylase 3AD-0089 (containing the amino acid substitution of A154V/M347A/R374F). The optical purity of tryptophan produced was analyzed by the procedure described below. The sample was loaded onto CROWNPAK CR(+) (Daicel Chemical Industries, Ltd.), and eluted using an $HClO_4$ solution (pH 2.0) as an elution buffer at the flow rate of 1.0 ml/min at 40° C. The elution was detected with the optical density at 280 nm. The retention times for the D and L forms were 16 and 19 minutes, respectively. The tryptophan produced was confirmed to be the D form because the optical purity was roughly estimated to be 100% e.e. Thus, the mutations introduced were found to exert no influence on the stereoselectivity (FIG. 2).

---

We claim:

1. A polypeptide having the activity of producing D-tryptophan in the presence of N-acetyl-DL-tryptophan, which comprises:

(a) an amino acid sequence of SEQ ID NO: 1, in which an amino acid residue has been substituted for at least one amino acid residue selected from the group consisting of alanine at position 154, methionine at position 347, and arginine at position 374; or (b) the amino acid sequence of (a), in which one or more amino acid residue other than amino acid residues at 154, 347, and 374 have been substituted, wherein the sequence is at least 95% identical to the amino acid sequence of SEQ ID NO:1.

2. The polypeptide according to claim 1, which comprises the amino acid sequence of SEQ ID NO: 1 which contains any one of amino acid substitutions selected from the group consisting of:

(A) substitution of alanine at position 154 with any one of amino acid selected from the group consisting of valine, cysteine, and threonine;

(B) substitution of methionine at position 347 with any one of amino acid selected from the group consisting of glycine, glutamine, serine, asparagine, alanine, isoleucine, and proline; and (C) substitution of arginine at position 374 with any one of amino acid selected from the group consisting of phenylalanine, lysine, leucine, tyrosine, histidine, isoleucine, and tryptophan.

3. The polypeptide according to claim 1, which comprises the amino acid sequence of SEQ ID NO: 1 which contains amino acid substitutions of two or more amino acid residues selected from the group consisting of alanine at position 154, methionine at position 347, and arginine at position 374.

4. The polypeptide according to claim 3, which comprises the amino acid sequence of SEQ ID NO: 1 which contains amino acid substitutions of alanine at position 154, methionine at position 347, and arginine at position 374.

5. The polypeptide according to claim 1, which hydrolyzes specifically N-acetyl-D-tryptophan from 120 g/l N-acetyl-DL-tryptophan as a substrate and thus produces D-tryptophan in 80% or higher yield.

6. A method for producing D-tryptophan, which comprises the steps of contacting N-acetyl-DL-tryptophan with at least one material selected from the group consisting of;

(a) a polypeptide according to claim 1;

(b) an isolated cell transformed with an expression vector comprising a polynucleotide encoding the polypeptide according to (a); and (c) a product of the transformed cell according to (b), wherein the product is a cell-free extract or an organic solvent extracted product and has the activity of producing D-tryptophan in the presence of N-acetyl-DL-tryptophan; and recovering the produced D-tryptophan.

7. The production method according to claim 6, wherein the concentration of N-acetyl-DL-tryptophan is 120 g/l or higher.

8. The polypeptide according to claim 1, wherein up to 10 amino acid residues other than amino acid residues at 154, 347, and 374 have been substituted.

* * * * *

SEQUENCE LISTING

<160> NUMBER OF SEQ ID NOS: 17

<210> SEQ ID NO 1
<211> LENGTH: 484
<212> TYPE: PRT
<213> ORGANISM: Alcaligenes denitrificans subsp. xylosoxydans MI-4

<400> SEQUENCE: 1

```
Met Ser Gln Ser Asp Ser Gln Pro Phe Asp Leu Leu Leu Ala Gly Gly
1               5                   10                  15

Thr Leu Ile Asp Gly Ser Asn Thr Pro Gly Arg Arg Ala Asp Leu Gly
            20                  25                  30

Val Arg Gly Asp Arg Ile Ala Ala Ile Gly Asp Leu Ser Asp Ala Ala
        35                  40                  45

Ala His Thr Arg Val Asp Val Ser Gly Leu Val Val Ala Pro Gly Phe
    50                  55                  60

Ile Asp Ser His Thr His Asp Asp Asn Tyr Leu Leu Arg Arg Arg Asp
65                  70                  75                  80

Met Thr Pro Lys Ile Ser Gln Gly Val Thr Thr Val Val Thr Gly Asn
                85                  90                  95

Cys Gly Ile Ser Leu Ala Pro Leu Ala His Ala Asn Pro Pro Ala Pro
            100                 105                 110

Leu Asp Leu Leu Asp Glu Gly Gly Ser Tyr Arg Phe Glu Arg Phe Ala
        115                 120                 125

Asp Tyr Leu Asp Ala Leu Arg Ala Thr Pro Ala Ala Val Asn Ala Ala
    130                 135                 140

Cys Met Val Gly His Ser Thr Leu Arg Ala Ala Val Met Pro Asp Leu
145                 150                 155                 160
```

-continued

```
Gln Arg Ala Ala Thr Asp Glu Glu Ile Ala Ala Met Arg Asp Leu Ala
                165                 170                 175
Glu Glu Ala Met Ala Ser Gly Ala Ile Gly Ile Ser Thr Gly Ala Phe
            180                 185                 190
Tyr Pro Pro Ala Ala Arg Ala Thr Glu Glu Ile Ile Glu Val Cys
        195                 200                 205
Arg Pro Leu Ser Ala His Gly Gly Ile Tyr Ala Thr His Met Arg Asp
    210                 215                 220
Glu Gly Glu His Ile Val Ala Ala Leu Glu Glu Thr Phe Arg Ile Gly
225                 230                 235                 240
Arg Glu Leu Asp Val Pro Val Val Ile Ser His His Lys Val Met Gly
                245                 250                 255
Gln Pro Asn Phe Gly Arg Ser Arg Glu Thr Leu Pro Leu Ile Glu Ala
            260                 265                 270
Ala Met Ala Arg Gln Asp Val Ser Leu Asp Ala Tyr Pro Tyr Val Ala
        275                 280                 285
Gly Ser Thr Met Leu Lys Gln Asp Arg Val Leu Leu Ala Gly Arg Thr
    290                 295                 300
Ile Ile Thr Trp Cys Lys Pro Phe Pro Glu Leu Ser Gly Arg Asp Leu
305                 310                 315                 320
Asp Glu Val Ala Ala Glu Arg Gly Lys Ser Lys Tyr Asp Val Val Pro
                325                 330                 335
Glu Leu Gln Pro Ala Gly Ala Ile Tyr Phe Met Met Asp Glu Pro Asp
            340                 345                 350
Val Gln Arg Ile Leu Ala Phe Gly Pro Thr Met Ile Gly Ser Asp Gly
        355                 360                 365
Leu Pro His Asp Glu Arg Pro His Pro Arg Leu Trp Gly Thr Phe Pro
    370                 375                 380
Arg Val Leu Gly His Tyr Ala Arg Asp Leu Gly Leu Phe Pro Leu Glu
385                 390                 395                 400
Thr Ala Val Trp Lys Met Thr Gly Leu Thr Ala Ala Arg Phe Gly Leu
                405                 410                 415
Ala Gly Arg Gly Gln Leu Gln Ala Gly Tyr Phe Ala Asp Leu Val Val
            420                 425                 430
Phe Asp Pro Ala Thr Val Ala Asp Thr Ala Thr Phe Glu His Pro Thr
        435                 440                 445
Glu Arg Ala Ala Gly Ile His Ser Val Tyr Val Asn Gly Ala Pro Val
    450                 455                 460
Trp Gln Glu Gln Ala Phe Thr Gly Gln His Ala Gly Arg Val Leu Ala
465                 470                 475                 480
Arg Thr Ala Ala
```

<210> SEQ ID NO 2
<211> LENGTH: 1455
<212> TYPE: DNA
<213> ORGANISM: Alcaligenes denitrificans subsp. xylosoxydans MI-4

<400> SEQUENCE: 2

```
atgtcccaat ccgattccca gcccttcgac ctgctgctcg cgggcggcac cctcatcgac    60
ggcagcaaca ccccggggcg gcgcgccgac ctgggcgtgc gcggcgaccg catcgccgcc   120
atcggcgatc tgtcggacgc cgccgcgcac acccgggtcg acgtgtcggg cctggtggtc   180
gcgcccggct tcatcgactc gcacacccac gacgacaact acctgctcag cgtcgcgac   240
atgacgccca agatctcgca gggcgtcacc acggtggtca cggcaattg cggcatcagc   300
```

-continued

```
ctggcgccgc tggcgcacgc caacccgccc gcccccctgg acctgctgga cgaaggcggt      360
tcttaccgtt tcgagcgctt cgccgactac ctggacgcgt tgcgggccac gccggcggcc      420
gtcaacgccg cctgcatggt gggccattca acgctgcgcg ccgcggtcat gccggacttg      480
cagcgcgccg ccaccgacga ggaaatcgcg gccatgcggg acctggccga ggaagccatg      540
gccagcggcg ccatcggcat ttcgaccggc gccttctacc cgcccgccgc ccgcgccacc      600
accgaagaga tcatcgaggt gtgccggccg ctgagcgcgc atggcggcat ctacgccacc      660
cacatgcgcg acgaaggcga gcacatcgtg gccgcgctgg aggaaaccct tcgcatcggc      720
cgcgagctgg acgtgccggt ggtgatctcg caccacaagg tcatgggcca gcccaatttc      780
ggccgctcgc gcgagacgct gccgctgatc gaggccgcca tggcgcgcca ggacgtctcg      840
ctggacgcgt atccctacgt ggccggctcc accatgctca agcaggaccg cgtgctgctg      900 gccgacgca ccatcatcac ctggtgcaag cccttcccg aactgagcgg gcgcgacctg       960
gatgaagtcg cggccgagcg cggcaaatcc aagtacgacg tggtgcccga gctgcagccg      1020
gccggcgcca tctacttcat gatggacgaa cccgacgtgc agcgcatcct ggcgttcggc      1080
ccgaccatga tcggctccga cggcctgccg cacgacgagc gcccgcatcc gcgcctgtgg      1140
ggcaccttcc gcgggtgct ggggcactat gcgcgcgacc tgggcctgtt cccgctggag       1200
acggcggtat ggaagatgac cggcctgacc gccgcgcgct cggcctggc cgggcgcggg      1260 cagctgcagg ccgggtactt cgccgacctg gtggtgttcg acccggccac ggtggccgat      1320
accgccacct tcgaacaccc taccgagcgc gccgccggca tccattccgt gtacgtcaac      1380
ggcgcgccgg tctggcaaga gcaggcgttc accggccagc atgccggccg cgtgctcgca      1440
cgcacggccg cctga                                                       1455
```

<210> SEQ ID NO 3
<211> LENGTH: 1455
<212> TYPE: DNA
<213> ORGANISM: Artificial
<220> FEATURE:
<223> OTHER INFORMATION: an artificially synthesized sequence

<400> SEQUENCE: 3

```
atgtctcaat ctgattcaca accttttgat ttactgttag ctggtggcac actgatcgat       60
ggtagtaaca ccccgggccg tcgcgcggac ctgggtgttc gtggcgatcg catcgcagcg      120
attggtgact tgagtgatgc tgcggcacat actcgtgtgg acgttagcgg cctggtggta      180
gctccaggtt tcatcgattc tcacacccat gacgataact acctgcttcg acgtcgcgac      240
atgaccccga aaatctccca gggcgttact accgtggtta ccgtaattg cggcatttca      300 ctggctccgc tggcgcacgc aaacccgccg gcgcctctcg atctgctgga cgaaggtggc      360
tcgtaccgtt tcgaacgctt tgctgattat ttagacgcgc tgcgtgcaac tccagccgct      420
gtgaacgcgg catgtatggt aggtcatagt accctgcgcg cggctgttat gccagatctg      480
cagcgtgcgg caaccgacga agagatcgca gctatgcgcg atctggcgga agaagcaatg      540
gcgtccggcg caattggtat ttctactggc gccttctacc cgccagcagc gcgtgctacc      600
acggaagaga tcatcgaagt gtgtcgaccg ctgagcgcgc acggtggcat ttacgcaact      660
catatgcgtg atgaaggtga acacatcgtt gcagctcttg aggaaaccct tcgcatcggc      720
cgtgaactgg atgtgccggt agttatttca catcacaaag tgatgggtca gcccaatttc      780
ggccgctcgc gtgaaaccct gccgctcatc gaggccgcaa tggcgcgcca ggacgttagt      840
```

```
ctggatgctt atccgtacgt ggcgggtagc actatgctga aacaggatcg tgtattactg      900
gccggccgca caatcattac ctggtgcaag ccattcccgg aactgtctgg tcgtgatttg      960
gacgaagttg cggctgaacg cggcaaatcc aaatacgatg tggttccgga gctgcaacct     1020
gctggtgcaa tctattttat gatggacgaa ccggatgtac agcgtatcct ggcgttcggc     1080
ccgactatga ttggttcaga cggccttcca catgatgaac gcccgcaccc gcgtctgtgg     1140
ggtaccttcc cacgggtact gggccattac gctcgtgacc tcggtctgtt tccgctggaa     1200
accgcggttt ggaaaatgac tggcttaacc gcagcgcgct tcggtctggc tggccgtggt     1260
cagctgcagg ccggctactt cgcagatttg gtggttttg acccggcgac cgtggctgat     1320
actgctacct tcgagcaccc aactgaacgc gcagcgggta tccattcggt atatgttaac     1380
ggagctccgg tgtggcaaga acaggcattt actggtcagc atgcaggtcg tgttcttgct     1440
cgtacagctg cataa                                                     1455
```

<210> SEQ ID NO 4
<211> LENGTH: 28
<212> TYPE: DNA
<213> ORGANISM: Artificial
<220> FEATURE:
<223> OTHER INFORMATION: Artificially Synthesized Primer Sequence

<400> SEQUENCE: 4
cttgatcgcc ccgccggaga tttccatg                                         28

<210> SEQ ID NO 5
<211> LENGTH: 26
<212> TYPE: DNA
<213> ORGANISM: Artificial
<220> FEATURE:
<223> OTHER INFORMATION: Artificially Synthesized Primer Sequence

<400> SEQUENCE: 5
gattgtaagg gctggcgccg ggctca                                           26

<210> SEQ ID NO 6
<211> LENGTH: 26
<212> TYPE: DNA
<213> ORGANISM: Artificial
<220> FEATURE:
<223> OTHER INFORMATION: Artificially Synthesized Primer Sequence

<400> SEQUENCE: 6
cgtcgtgggt gtgcgagtcg atgaag                                           26

<210> SEQ ID NO 7
<211> LENGTH: 17
<212> TYPE: DNA
<213> ORGANISM: Artificial
<220> FEATURE:
<223> OTHER INFORMATION: Artificially Synthesized Primer Sequence

<400> SEQUENCE: 7
catggcttcc tcggcca                                                     17

<210> SEQ ID NO 8
<211> LENGTH: 18
<212> TYPE: DNA
<213> ORGANISM: Artificial
<220> FEATURE:
<223> OTHER INFORMATION: Artificially Synthesized Primer Sequence

<400> SEQUENCE: 8

-continued gtcatgccgg acttgcag                                              18

<210> SEQ ID NO 9
<211> LENGTH: 21
<212> TYPE: DNA
<213> ORGANISM: Artificial
<220> FEATURE:
<223> OTHER INFORMATION: Artificially Synthesized Primer Sequence

<400> SEQUENCE: 9
ggttcgtcca tcatgaagta g                                          21

<210> SEQ ID NO 10
<211> LENGTH: 19
<212> TYPE: DNA
<213> ORGANISM: Artificial
<220> FEATURE:
<223> OTHER INFORMATION: Artificially Synthesized Primer Sequence

<400> SEQUENCE: 10
atccaagtac gacgtggtg                                             19

<210> SEQ ID NO 11
<211> LENGTH: 49
<212> TYPE: DNA
<213> ORGANISM: Artificial
<220> FEATURE:
<223> OTHER INFORMATION: Artificially Synthesized Primer Sequence

<400> SEQUENCE: 11
gtcgaattca tacatgtctc aatcagattc tcaaccattc gacctgctg            49

<210> SEQ ID NO 12
<211> LENGTH: 48
<212> TYPE: DNA
<213> ORGANISM: Artificial
<220> FEATURE:
<223> OTHER INFORMATION: Artificially Synthesized Primer Sequence

<400> SEQUENCE: 12
ctgaagcttc tagattatgc agcagtacgt gcaagaacgc ggccggca             48

<210> SEQ ID NO 13
<211> LENGTH: 29
<212> TYPE: DNA
<213> ORGANISM: Artificial
<220> FEATURE:
<223> OTHER INFORMATION: Artificially Synthesized Primer Sequence

<400> SEQUENCE: 13
atcgatggta gtaacacccc gggccgtcg                                  29

<210> SEQ ID NO 14
<211> LENGTH: 34
<212> TYPE: DNA
<213> ORGANISM: Artificial
<220> FEATURE:
<223> OTHER INFORMATION: Artificially Synthesized Primer Sequence
<220> FEATURE:
<221> NAME/KEY: misc_feature
<222> LOCATION: (21)..(23)
<223> OTHER INFORMATION: n indicates any one of g, a, c or t

<400> SEQUENCE: 14
tgcagatctg gcataacagc nnngcgcagg gtac                            34

```
<210> SEQ ID NO 15
<211> LENGTH: 32
<212> TYPE: DNA
<213> ORGANISM: Artificial
<220> FEATURE:
<223> OTHER INFORMATION: Artificially Synthesized Primer Sequence

<400> SEQUENCE: 15
accgctgagc gcgcacggtg gcatttacgc aa                                32

<210> SEQ ID NO 16
<211> LENGTH: 38
<212> TYPE: DNA
<213> ORGANISM: Artificial
<220> FEATURE:
<223> OTHER INFORMATION: Artificially Synthesized Primer Sequence
<220> FEATURE:
<221> NAME/KEY: misc_feature
<222> LOCATION: (24)..(26)
<223> OTHER INFORMATION: n indicates any one of g, a, c or t

<400> SEQUENCE: 16
cgctgtacat ccggttcgtc catnnnaaaa tagattgc                          38

<210> SEQ ID NO 17
<211> LENGTH: 41
<212> TYPE: DNA
<213> ORGANISM: Artificial
<220> FEATURE:
<223> OTHER INFORMATION: Artificially Synthesized Primer Sequence
<220> FEATURE:
<221> NAME/KEY: misc_feature
<222> LOCATION: (28)..(30)
<223> OTHER INFORMATION: n indicates any one of g, a, c or t

<400> SEQUENCE: 17
gaaggtaccc cacagacgcg ggtgcggnnn ttcatcatgt g                      41
```